US010711065B2

(12) United States Patent
Keefe et al.

(10) Patent No.: US 10,711,065 B2
(45) Date of Patent: Jul. 14, 2020

(54) ANTI-FLT-1 ANTIBODIES IN TREATING BRONCHOPULMONARY DYSPLASIA

(71) Applicant: SHIRE HUMAN GENETIC THERAPIES, INC., Lexington, MA (US)

(72) Inventors: Dennis Keefe, Lexington, MA (US); Hans De Haard, Zwijnaarde (BE)

(*) Notice: Subject to any disclaimer, the term of this patent is extended or adjusted under 35 U.S.C. 154(b) by 0 days.

(21) Appl. No.: 15/565,009

(22) PCT Filed: Apr. 7, 2016

(86) PCT No.: PCT/US2016/026436
§ 371 (c)(1),
(2) Date: Oct. 6, 2017

(87) PCT Pub. No.: WO2016/164579
PCT Pub. Date: Oct. 13, 2016

(65) Prior Publication Data
US 2018/0100017 A1 Apr. 12, 2018

Related U.S. Application Data

(60) Provisional application No. 62/144,247, filed on Apr. 7, 2015.

(51) Int. Cl.
C07K 16/28 (2006.01)
A61P 11/00 (2006.01)
A61K 39/00 (2006.01)

(52) U.S. Cl.
CPC .......... C07K 16/2863 (2013.01); A61P 11/00 (2018.01); A61K 2039/505 (2013.01); A61K 2039/54 (2013.01); A61K 2039/545 (2013.01); A61K 2039/55 (2013.01); C07K 2317/22 (2013.01); C07K 2317/24 (2013.01); C07K 2317/33 (2013.01); C07K 2317/34 (2013.01); C07K 2317/515 (2013.01); C07K 2317/55 (2013.01); C07K 2317/565 (2013.01); C07K 2317/569 (2013.01); C07K 2317/70 (2013.01); C07K 2317/74 (2013.01); C07K 2317/76 (2013.01); C07K 2317/92 (2013.01); C07K 2317/94 (2013.01)

(58) Field of Classification Search
CPC ............ C07K 16/2863; C07K 2317/24; C07K 2317/55; C07K 2317/76; C07K 2317/515; C07K 2317/565; A61K 2039/505; A61P 11/00
See application file for complete search history.

(56) References Cited

U.S. PATENT DOCUMENTS 7,335,362 B2  2/2008  Karumanchi

FOREIGN PATENT DOCUMENTS

| WO | 2004/008946 A2 | 1/2004 |
| WO | WO2006/055809 A2 | 5/2006 |
| WO | 2006/076467 A2 | 7/2006 |
| WO | 2010/075475 A1 | 7/2010 |
| WO | 2012/109282 A2 | 8/2012 |
| WO | 2014/117160 A1 | 7/2014 |
| WO | WO2014/150314 A1 | 9/2014 |

OTHER PUBLICATIONS

Altschul et al., "Basic local alignment search tool", J. Mol. Biol., 215(3): 403-410 (1990).
Altschul et al., "Local alignment statistics", Methods in Enzymology, vol. 266, pp. 460-480 (1996).
Altschul et al., "Gapped BLAST and PSI-BLAST: a new generation of protein database search programs", Nucleic Acids Res., 25:3389-3402 (1997).
Barbas et al., "In vitro evolution of a neutralizing human antibody to human immunodeficiency virus type 1 to enhance affinity and broaden strain cross-reactivity", Proc. Nat. Acad. Sci. USA, 91(9):3809-3813 (1994).
Bird et al., "Single-chain antigen-binding proteins", Science, 242(4877): 423-6 (1988).
Cooney et al., "The radial alveolar count method of Emery and Mithal: a reappraisal 1—postnatal lung growth", Thorax, 37(8): 572-9 (1982).
Cooney et al., "The radial alveolar count method of Emery and Mithal: a reappraisal 2—intrauterine and early postnatal lung growth", 37(8): 580-3 (1982).
Hawkins et al., "Selection of phage antibodies by binding affinity. Mimicking affinity maturation", J. Mol. Biol., 226: 389-896 (1992).
Huston et al., "Protein engineering of antibody binding sites: recovery of specific activity in an anti-digoxin single-chain Fv analogue produced in *Escherichia coli*", Proc. Natl. Acad. Sci. USA, 85: 5879-5883 (1988).
Jackson et al., "In vitro antibody maturation. Improvement of a high affinity, neutralizing antibody against IL-1 beta",J. Immunol., 154(7): 3310-9 (1995).
Jönsson, U. et al., "Introducing a biosensor based technology for real-time biospecific interaction analysis", Ann Biol Clin (Paris), 51(1): 19-26 (1993).
Jönsson, U. et al., "Real-time biospecific interaction analysis using surface plasmon resonance and a sensor chip technology", Biotechniques, 11(5): 620-7 (1991).
Johnsson, B. et al., "Comparison of methods for immobilization to carboxymethyl dextran sensor surfaces by analysis of the specific activity of monoclonal antibodies", J Mol Recognit, 8(1-2): 125-31 (1995).

(Continued)

Primary Examiner — Ruixiang Li
(74) Attorney, Agent, or Firm — Proskauer Rose LLP; Fangli Chen

(57) ABSTRACT

The present invention provides, among other things, methods and compositions for treating chronic lung disorders, in particular, bronchopulmonary dysplasia (BPD). In some embodiments, a method according to the present invention includes administering to an individual who is suffering from or susceptible to BPD an effective amount of an anti-Flt-1 antibody, or antigen binding fragment thereof, such that at least one symptom or feature of BPD is reduced in intensity, severity, or frequency, or has delayed onset.

16 Claims, No Drawings
Specification includes a Sequence Listing.

(56) References Cited

OTHER PUBLICATIONS

Johnsson, B. et al., "Immobilization of proteins to a carboxymethyldextran-modified gold surface for biospecific interaction analysis in surface plasmon resonance sensors", Anal Biochem., 198(2): 268-77 (1991).

Marks et al., "By-passing immunization: building high affinity human antibodies by chain shuffling", BioTechnology, 10 (7): 779-783 (1992).

Peisl et al., "Treatment With an Anti-SFLT-1 Monoclonal Antibody Improves Lung Structure and Prevents Pulmonary Hypertension in an Experimental Model of Bronchopulmonary Dysplasia Due to Preeclampsia in Infant Rats", Biosis, Biosciences Information Service, Philadelphia, PA, US, (2016).

Peisl et al., "Treatment With an Anti-SFLT-1 Monoclonal Antibody Improves Lung Structure and Prevents Pulmonary Hypertension in an Experimental Model of Bronchopulmonary Dysplasia Due to Preeclampsia in Infant Rats", Journal of Investigative Medicine, Western Regional Meeting of the American-Federation-For-Medical-Research, 64(1): 156 (2016).

Schier et al., "Identification of functional and structural amino-acid residues by parsimonious mutagenesis", Gene, 169 (2): 147-155 (1995).

Tang et al., "Excess soluble vascular endothelial growth factor receptor-1 in amniotic fluid impairs lung growth in rats: linking preeclampsia with bronchopulmonary dysplasia", Am J Physiol Lung Cell Mol Physiol., 302(1): L36-46 (2012).

Yelton et al., "Affinity maturation of the BR96 anti-carcinoma antibody by codon-based mutagenesis", J. Immunol., 155 (4): 1994-2004 (1995).

Ward et al., "Binding activities of a repertoire of single immunoglobulin variable domains secreted from *Escherichia coli*", Nature, 341(1642):544-546 (1989).

Ennen, J. P. et al., "Vascular-targeted therapies for Duchene muscular dystrophy", Skeletal Muscle, vol., 3, No. 1, Apr. 2013, 12 pages.

Gien, J. et al., "Pathogenesis and Treatment of Bronchopulmonary Dysplasia", Curr. Opin. Pediatr., Jun. 2011, vol. 23, No. 3, pp. 304-313.

Mcevoy, C. T. et al., "The Natural History of Bronchopulmonary Dysplasia (BPD): The Case for Primary Prevention", Clin. Perinatol., Dec. 2015, vol. 42, No. 4, pp. 911-931.

Messina, S. et al., "VEGF overexpression via adeno-associated virus gene transfer promotes skeletal muscle regeneration and enhances muscle function in mdx mice", The Faseb Journal, vol. 21, No. 13, Nov. 1, 2007, pp. 3737-3746.

Sanz, L. et al., "Antibodies and Gene Therapy: teaching old 'magic bullets' new tricks", Trends in Immunology, vol. 25, No. 2, Feb. 1, 2004, pp. 85-91.

Sibai, B. et al., "Pre-eclampsia", Lancet, (Feb. 26, 2005), vol. 365, pp. 785-789.

Shimizu-Motohashi, Y. et al., "Angiogenesis as a novel therapeutic strategy for Duchenne muscular dystrophy through decreased ischemia and increased satellite cells", Frontiers in Physiology, vol. 5, No. 50, Jan. 27, 2014, pp. 1-17.

Verma, M. et al., "Flt-1 haploinsufficiency ameliorates muscular dystrophy phenotype by developmentally increased vasculature in mdx mice", Human Molecular Genetics, Vo. 19, No. 21, Aug. 12, 2010, pp. 4145-4159.

Wu, Y. et al., "Anti-Vascular Endothelial Growth Factor Receptor-1 Antagonist Antibody as a Therapeutic Agent for Cancer", Clinical Cancer Research, vol. 12, No. 21, Nov. 1, 2006, pp. 6573-6584.

ANTI-FLT-1 ANTIBODIES IN TREATING BRONCHOPULMONARY DYSPLASIA

RELATED APPLICATIONS

This application is a 35 U.S.C. § 371 National Stage Application of International Application No. PCT/US16/26436, filed Apr. 7, 2016, which claims priority to U.S. Provisional Application Ser. No. 62/144,247, filed Apr. 7, 2015, the disclosure of which is hereby incorporated by reference.

INCORPORATION-BY-REFERENCE OF SEQUENCE LISTING

The content of the text file named "SHR-1236US_ST25.txt", which was created on Oct. 6, 2017 and is 169 KB in size, is hereby incorporated by reference in its entirety.

BACKGROUND

Bronchopulmonary dysplasia (BPD) is a severe, chronic lung disease that primarily affects premature infants. Premature infants can develop BPD after their lungs have been damaged from the use of supplemental oxygen and mechanical breathing aids. Infants with BPD have inflammation and scarring in the lungs and in severe cases, are at high risk for prolonged need for ventilator or oxygen support, pulmonary hypertension, recurrent respiratory infections, abnormal lung function, exercise intolerance, late neuro-developmental conditions, and even death.

Many infants with BPD recover and improve with time, however, these children are at increased risk of developing further complications, including asthma and viral pneumonia. And while most infants survive, some infants with very severe BPD will still die from the disease even after months of care.

SUMMARY OF THE INVENTION

The present invention provides, among other things, improved methods and compositions for treating chronic lung disorders, in particular, bronchopulmonary dysplasia (BPD), based on anti-Flt-1 antibody therapy. As described in the Examples below, the invention is, in part, based on the discovery that anti-Flt-1 antibodies, or antigen binding fragments thereof, can inhibit VEGF and other ligands from binding to the Flt-1 receptor, thereby increasing the amount VEGF and/or other ligands available to bind to VEGF receptors. This increased binding can induce a pro-angiogenic effect that increases capillary density and facilitates reduction of fibrosis and inflammation, and mitigation of symptoms and features associated with BPD. Indeed, as shown in the Examples, the present inventors have demonstrated that administration of an anti-Flt-1 antibody improves measures of lung pathology in BPD animal models. Therefore, the present invention provides safe and effective antibody-based therapeutics for the treatment of BPD.

In one aspect, the present invention provides methods of treating bronchopulmonary dysplasia (BPD) comprising administering to an individual in need of treatment an effective amount of an anti-Flt-1 antibody or antigen binding fragment thereof, wherein the anti-Flt-1 antibody or antigen-binding fragment thereof comprises one or more complementarity determining regions (CDR) selected from the group consisting of: a variable light (VL) chain CDR1 defined by an amino acid sequence having at least 80% identity to any one of SEQ ID NO:19 to SEQ ID NO:21, a VL CDR2 defined by an amino acid sequence having at least 80% identity to any one of SEQ ID NO:22 to SEQ ID NO:24, a VL CDR3 defined by an amino acid sequence having at least 80% identity to any one of SEQ ID NO:25 to SEQ ID NO:34, a variable heavy (VH) chain CDR1 defined by an amino acid sequence having at least 80% identity to any one of SEQ ID NO:1 to SEQ ID NO:4, a VH CDR2 defined by an amino acid sequence having at least 80% identity to any one of SEQ ID NO:5 to SEQ ID NO:14, and a VH CDR3 defined by an amino acid sequence having at least 80% identity to any one of SEQ ID NO:15 to SEQ ID NO:18.

In some embodiments, one or more CDRs comprise the VL CDR3 defined by the amino acid sequence having at least 80% identity to any one of SEQ ID NO:25 to SEQ ID NO:34; and the VH CDR3 defined by the amino acid sequence having at least 80% identity to any one of SEQ ID NO:15 to SEQ ID NO:18.

In some embodiments, one or more CDRs comprise the VL CDR1 defined by the amino acid sequence having at least 80% identity to any one of SEQ ID NO:19 to SEQ ID NO:21, the VL CDR2 defined by the amino acid sequence having at least 80% identity to any one of SEQ ID NO:22 to SEQ ID NO:24, and the VL CDR3 defined by the amino acid sequence having at least 80% identity to any one of SEQ ID NO:25 to SEQ ID NO:34.

In some embodiments, one or more CDRs comprise the VH CDR1 defined by the amino acid sequence having at least 80% identity to any one of SEQ ID NO:1 to SEQ ID NO:4, the VH CDR2 defined by the amino acid sequence having at least 80% identity to any one of SEQ ID NO:5 to SEQ ID NO:14, and the VH CDR3 defined by the amino acid sequence having at least 80% identity to any one of SEQ ID NO:15 to SEQ ID NO:18.

In some embodiments, an anti-Flt-1 antibody or antigen-binding fragment thereof comprises a VL chain comprising the VL CDR1, VL CDR2, and VL CDR3 defined by the amino acid sequence of SEQ ID NO:19, SEQ ID NO:22, and SEQ ID NO:25, respectively.

In some embodiments, an anti-Flt-1 antibody or antigen-binding fragment thereof comprises a VL chain comprising the VL CDR1, VL CDR2, and VL CDR3 defined by the amino acid sequence of SEQ ID NO:20, SEQ ID NO:23, and SEQ ID NO:25, respectively.

In some embodiments, an anti-Flt-1 antibody or antigen-binding fragment thereof comprises a VL chain comprising the VL CDR1 and VL CDR2 defined by the amino acid sequence of SEQ ID NO:21 and SEQ ID NO:24, respectively, and the VL CDR3 defined by the amino acid sequence of SEQ ID NO:26, SEQ ID NO:27, SEQ ID NO:28, SEQ ID NO:29, SEQ ID NO:30, SEQ ID NO:31, SEQ ID NO:32, SEQ ID NO:33, or SEQ ID NO:34.

In some embodiments, a VL chain comprising the VL CDR1, VL CDR2, and VL CDR3 is defined by the amino acid sequence of SEQ ID NO:21, SEQ ID NO:24, and SEQ ID NO:32, respectively.

In some embodiments, an anti-Flt-1 antibody or antigen-binding fragment thereof comprises a VH chain comprising the VH CDR1, VH CDR2, and VH CDR3 is defined by the amino acid sequences of SEQ ID NO:1, SEQ ID NO:5, and SEQ ID NO:15, respectively.

In some embodiments, an anti-Flt-1 antibody or antigen-binding fragment thereof comprises a VH chain comprising the VH CDR1, VH CDR2, and VH CDR3 defined by the amino acid sequences of SEQ ID NO:2, SEQ ID NO:6, and SEQ ID NO:16, respectively.

In some embodiments, an anti-Flt-1 antibody or antigen-binding fragment thereof comprises a VH chain comprising the VH CDR1, VH CDR2, and VH CDR3 defined by the amino acid sequences of SEQ ID NO:2, SEQ ID NO:10, and SEQ ID NO:18, respectively.

In some embodiments, an anti-Flt-1 antibody or antigen-binding fragment thereof comprises a VH chain comprising the VH CDR1 and the VH CDR3 defined by the amino acid sequences of SEQ ID NO:2 and SEQ ID NO:17, respectively, and the VH CDR2 defined by the amino acid sequence of SEQ ID NO:7, SEQ ID NO:8, SEQ ID NO:13 or SEQ ID NO:14.

In some embodiments, an anti-Flt-1 antibody or antigen-binding fragment thereof comprises a VH chain comprising the VH CDR1 and the VH CDR3 defined by the amino acid sequences of SEQ ID NO:3 and SEQ ID NO:17, respectively, and the VH CDR2 defined by the amino acid sequence of SEQ ID NO:9, SEQ ID NO:11 or SEQ ID NO:12.

In some embodiments, an anti-Flt-1 antibody or antigen-binding fragment thereof comprises a VH chain comprising the VH CDR1, VH CDR2, and VH CDR3 defined by the amino acid sequences of SEQ ID NO:4, SEQ ID NO:9, and SEQ ID NO:17, respectively.

In some embodiments, an anti-Flt-1 antibody or antigen-binding fragment thereof comprises a VH chain comprising the VH CDR1, VH CDR2, and VH CDR3 defined by the amino acid sequences of SEQ ID NO:3, SEQ ID NO:12, and SEQ ID NO:17, respectively.

In another aspect, the present invention provides methods of treating bronchopulmonary dysplasia (BPD) comprising administering to an individual in need of treatment an effective amount of an anti-Flt-1 antibody or antigen binding fragment thereof, wherein an anti-Flt-1 antibody or antigen-binding fragment thereof comprises: (i) a light chain variable (VL) region comprising an amino acid sequence having at least 80% identity to any one of SEQ ID NO:49 to SEQ ID NO:61, and/or (ii) a heavy chain variable (VH) region comprising an amino acid sequence having at least 80% identity to any one of SEQ ID NO:35 to SEQ ID NO:48.

In some embodiments, the VL region comprises the amino acid sequence of SEQ ID NO:60 and the VH region comprises the amino acid sequence of SEQ ID NO:45.

In some embodiments, an anti-Flt-1 antibody or antigen-binding fragment thereof further comprises a heavy chain constant region comprising an amino acid sequence having at least 80% identity to any one of SEQ ID NO:87 to SEQ ID NO:89.

In another aspect, the present invention provides methods of treating bronchopulmonary dysplasia (BPD) comprising administering to an individual in need of treatment an effective amount of an anti-Flt-1 antibody or antigen binding fragment thereof, wherein the anti-Flt-1 antibody or antigen-binding fragment thereof comprises: (i) a light chain comprising an amino acid sequence having at least 80% identity to any one of SEQ ID NO:75 to SEQ ID NO:86, and/or (ii) a heavy chain comprising an amino acid sequence having at least 80% identity to any one of SEQ ID NO:62 to SEQ ID NO:74. In some embodiments, the light chain comprises the amino acid sequence of SEQ ID NO:76 and the heavy chain comprises the amino acid sequence of SEQ ID NO:71.

In some embodiments, an anti-Flt-1 antibody or antigen-binding fragment thereof is selected from the group consisting of IgG, F(ab')$_2$, F(ab)$_2$, Fab', Fab, ScFvs, diabodies, triabodies and tetrabodies. In some embodiments, the anti-Flt-1 antibody or antigen-binding fragment thereof is IgG. In some embodiments, the anti-Flt-1 antibody or antigen-binding fragment thereof is IgG1.

In some embodiments, an anti-Flt-1 antibody or antigen-binding fragment thereof is a monoclonal antibody. In some embodiments, an anti-Flt-1 antibody or antigen-binding fragment thereof is a humanized monoclonal antibody. In some embodiments, the humanized monoclonal antibody contains a human Fc region. In some embodiments, the Fc region contains one or more mutations that enhance the binding affinity between the Fc region and the FcRn receptor such that the in vivo half-life of the antibody is prolonged.

In some embodiments, an Fc region contains one or more mutations at positions corresponding to Leu 234, Leu 235 and/or Gly 237 of human IgG1.

In some embodiments, an anti-Flt-1 antibody or antigen-binding fragment thereof does not bind to VEGFR2 and/or VEGFR3.

In some embodiments, an anti-Flt-1 antibody or antigen-binding fragment thereof does not bind to a mouse or monkey Flt-1.

In another aspect, the present invention provides methods of treating bronchopulmonary dysplasia (BPD) comprising administering to an individual in need of treatment an effective amount of an anti-Flt-1 antibody or antigen binding fragment thereof, wherein the anti-Flt-1 antibody or antigen-binding fragment thereof recognizes a peptide comprising an amino acid sequence corresponding to positions 139 to 148, positions 139 to 153, positions 178 to 206, positions 199 to 204 and positions 128 to 138 of SEQ ID NO:90, or a fragment thereof. In some embodiments, the peptide consists of the amino acid sequence corresponding to positions 130 to 138, positions 141 to 148, positions 141 to 153 and positions 193 to 206 of SEQ ID NO:90.

In some embodiments, an individual is an infant who is suffering from or susceptible to BPD. In some embodiments, an individual is pregnant with a fetus who is suffering from or susceptible to BPD.

In some embodiments, an anti-Flt-1 antibody or antigen binding fragment thereof is administered parenterally. In some embodiments, the parenteral administration is selected from intravenous, intradermal, intrathecal, inhalation, transdermal (topical), intraocular, intramuscular, subcutaneous, pulmonary delivery, and/or transmucosal administration. In some embodiments, the parenteral administration is intravenous administration.

In some embodiments, an anti-Flt-1 antibody or antigen binding fragment thereof is administered orally.

In some embodiments, an anti-Flt-1 antibody or antigen binding fragment thereof is administered bimonthly, monthly, triweekly, biweekly, weekly, daily, or at variable intervals.

In some embodiments, an anti-Flt-1 antibody or antigen binding fragment thereof is delivered to one or more target tissues selected from lungs and heart In some embodiments, an anti-Flt-1 antibody or antigen binding fragment thereof is delivered to the lungs. In some embodiments, an anti-Flt-1 antibody, or an antigen binding fragment thereof, is delivered to the heart.

In some embodiments, administration of the anti-Flt-1 antibody or antigen binding fragment thereof results in growth of healthy lung tissue, decreased lung inflammation, increased alveologenesis, increased angiogenesis, improved structure of pulmonary vascular bed, reduced lung scarring, improved lung growth, reduced respiratory insufficiency, improved exercise tolerance, reduced adverse neurological outcome, and/or improved pulmonary function relative to a control.

In some embodiments, the present invention provides a method further comprising co-administering at least one additional agent or therapy selected from a surfactant, oxygen therapy, ventilator therapy, a steroid, vitamin A, inhaled nitric oxide, high calorie nutritional formulation, a diuretic, and/or a bronchodilator.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Definitions

In order for the present invention to be more readily understood, certain terms are first defined below. Additional definitions for the following terms and other terms are set forth throughout the specification.

Affinity: As is known in the art, "affinity" is a measure of the tightness with a particular ligand binds to its partner. In some embodiments, the ligand or partner is Flt-1. In some embodiments, the ligand or partner is soluble Flt-1. In some embodiments, the ligand or partner is a recombinant Flt-1. In a particular embodiment the ligand or partner is human sFlt-1. In a particular embodiment, the ligand or partner is a recombinant sFlt-1. In other embodiments, the ligand or partner is an anti-Flt-1 antibody. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Affinity matured (or affinity matured antibody): As used herein, the term "affinity matured" or "affinity matured antibody", refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., Bio-Technology 10:779-783 (1992) describes affinity maturation by $V_H$ and $V_L$ domain shuffling. Random mutagenesis of CDR and/or framework residues is described by: Barbas et al. Proc. Nat. Acad. Sci. U.S.A. 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin isotype, including any of the human isotypes: IgG, IgM, IgA, IgD, and IgE. In certain embodiments, an antibody may be a member of the IgG immunoglobulin class (e.g., IgG1, IgG2, IgG3, etc). In some embodiments, an antibody may be a human antibody. In some embodiments, an antibody may be a humanized antibody.

As is known by those of ordinary skill in the art, antibodies produced in nature are typically comprised of four polypeptide chains, two heavy (H) chains and two light (L) chains interconnected by disulfide bonds. Each heavy and light chain is comprised of a variable region (abbreviated herein as HCVR, VH or $V_H$ and LCVR, VL or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The binding regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antigen binding portion: As used herein, the term "antigen-binding portion" or "antigen-binding fragment" refers to one or more fragments or portions of an antibody that retain the ability to specifically bind to an antigen (e.g., Flt-1). Examples of antigen-binding portions include (i) a Fab fragment, a monovalent fragment consisting of the $V_H$, $V_L$, $C_H1$ and $C_L$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; (vi) an isolated complementarity determining region (CDR); (vii) a Fab' fragment, which is essentially a Fab with part of the hinge region; (viii) a nanobody, a heavy chain variable region containing a single variable domain and two constant domains. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). An antigen-binding fragment of an antibody may optionally comprise a single chain antibody fragment. Alternatively or additionally, an antigen-binding fragment of an antibody may comprise multiple chains which are linked together, for example, by disulfide linkages. An antigen-binding fragment of an antibody may optionally comprise a multimolecular complex. A functional antibody fragment typically comprises at least about 50 amino acids and more typically comprises at least about 200 amino acids.

In some embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen.

Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, and recombinant production. The fragments are screened for utility in the same manner as are intact antibodies.

Amelioration: As used herein, the term "amelioration" is meant the prevention, reduction or palliation of a state, or improvement of the state of a subject. Amelioration includes, but does not require complete recovery or complete prevention of a disease condition.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the binding of one or more VEGF ligands, is considered to be biologically active.

Carrier or diluent: As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Chimeric antibody: As used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody."

CDR: As used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dysfunction: As used herein, the term "dysfunction" refers to an abnormal function. Dysfunction of a molecule (e.g., a protein) can be caused by an increase or decrease of an activity associated with such molecule. Dysfunction of a molecule can be caused by defects associated with the molecule itself or other molecules that directly or indirectly interact with or regulate the molecule.

Epitope: A used herein, includes any moiety that is specifically recognized by an immunoglobulin (e.g., antibody, antibody fragment thereof, receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms as groups are physically separated from one another when the antigen adopts an alternative conformation (e.g., is linearized).

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, Va.). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

Framework or framework region: As used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties that are similar to that of the substituted amino acid. Desirable similar chemico-physical properties include similarities in charge, bulkiness, hydrophobicity, hydrophilicity, and the like.

Fusion protein: As used herein, the term "fusion protein" or "chimeric protein" refers to a protein created through the joining of two or more originally separate proteins, or portions thereof. In some embodiments, a linker or spacer will be present between each protein.

Half-life: As used herein, the term "half-life" is the time required for a quantity such as protein concentration or activity to fall to half of its value as measured at the beginning of a time period.

Human antibody: as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Human monoclonal antibody: As used herein, is intended to refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heave chain transgene and a light chain transgene fused to an immortalized cell.

Humanized: As is known in the art, the term "humanized" is commonly used to refer to antibodies (or antibody components) whose amino acid sequence includes $V_H$ and $V_L$ region sequences from a reference antibody raised in a non-human species (e.g., a mouse, a llama), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody (e.g., a mouse, a llama). A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Hypertrophy: As used herein the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subjects) in the absence of the treatment described herein. A "control subject" is a subject afflicted with the same form of disease as the subject being treated, who is about the same age as the subject being treated.

Inhibition: As used herein, the terms "inhibition," "inhibit" and "inhibiting" refer to processes or methods of decreasing or reducing activity and/or expression of a protein or a gene of interest. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated Antibody: As used herein, the term "isolated antibody" is intended to refer to an antibody that is substantially free of other antibodies having different antigenic specificities (e.g., an isolated antibody that specifically binds to Flt-1). Moreover, an isolated antibody may be substantially free of other cellular material and/or chemicals.

$K_a$: As used herein, refers to the association rate of a particular antibody-antigen interaction, whereas the term "$K_d$," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. A preferred method for determining the $K_D$ of an antibody is by using surface plasmon resonance, preferably using a biosensor system such as a BIAcore® system.

Light-chain reshuffling: As used herein, the term "light-chain reshuffling" is intended to refer to an affinity maturation step where the heavy chain sequence is kept constant and a library of light chain sequences is generated. The light chain library is screened against the heavy chain to identify antibodies with improved binding affinity. The improved binding affinity may be in the nanomolar or picomolar ranges.

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Monoclonal antibody: As used herein, the term "monoclonal antibody" is intended to refer to a preparation of antibody molecules of a single molecular composition. A monoclonal antibody composition displays a single binding specificity and affinity for a particular epitope.

Pharmaceutically acceptable: As used herein, the term "pharmaceutically acceptable" refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, the term "polypeptide" refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: As used herein, the term "protein" refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., BPD). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., BPD). In some embodiments a reference sample or group of reference samples are from individuals comparable to a particular individual. In some embodiments, relative risk is 0, 1, 2, 3, 4, 5, 6, 7, 8, 9, 10, or more.

Selective binding: As used herein, "selective binding", "selectively binds" "specific binding", or "specifically binds" refers, with respect to a binding moiety and a target, preferential association of a binding moiety to a target and not to an entity that is not the target. A certain degree of non-specific binding may occur between a binding moiety and a non-target. In some embodiments, a binding moiety selectively binds a target if binding between the binding moiety and the target is greater than 2-fold, greater than 5-fold, greater than 10-fold, or greater than 100-fold as compared with binding of the binding moiety and a non-target. In some embodiments, a binding moiety selectively binds a target if the binding affinity is less than about $10^{-5}$ M, less than about $10^{-6}$ M, less than about $10^{-7}$ M, less than about $10^{-8}$M, or less than about $10^{-9}$M.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: As used herein, the phrase "substantial homology refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: As used herein, the phrase "substantial identity" is used to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Surface plasmon resonance: As used herein, refers to an optical phenomenon that allows for the analysis of specific binding interactions in real-time, for example through detection of alterations in protein concentrations within a biosensor matrix, such as by using a Biacore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, BPD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as BPD. In some embodiments, target tissues include those tissues that display disease-associated pathology, symptom, or feature, including but not limited to lung inflammation, lung scarring, impaired lung growth, early lung injury, prolonged respiratory insufficiency, lung infections, exercise intolerance, and adverse neurological outcome.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating chronic lung disorders, in particular, bronchopulmonary dysplasia (BPD), based on the use of anti-Flt-1 antibodies, or antigen binding fragments thereof, as therapeutics for treating BPD. In some embodiments, the present invention provides methods of treating BPD including administering to an individual who is suffering from or susceptible to BPD an effective amount of an Flt-1 antibody or antigen binding fragment thereof such that at least one symptom or feature of BPD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Bronchopulmonary Dysplasia (BPD)

With the introduction of surfactant therapy, maternal steroids, new ventilator strategies, aggressive management of the patent ductus arteriosus, improved nutrition, and other treatments, the clinical course and outcomes of premature newborns with RDS have dramatically changed over the past 30 years. It has recently been demonstrated that about two thirds of infants who develop BPD have only mild respiratory distress at birth. This suggests that developmental timing of lung injury is a critical factor in the etiology of BPD.

In parallel with this changing epidemiologic and clinical pattern, key features of lung histology in BPD have also changed. There is now growing recognition that infants with persistent lung disease after premature birth have a different clinical course and pathology than was traditionally observed in infants dying with BPD during this presurfactant era. The classic progressive stages that first characterized BPD are often absent owing to changes in clinical management, and BPD has clearly changed from being predominantly defined by the severity of acute lung injury to its current characterization, which is primarily defined by a disruption of distal lung growth. Thus, the so-called new BPD of the postsurfactant period represents inhibition of lung development with altered lung structure, growth, and function of the distal airspaces and vasculature. Physiologically, this suggests a marked reduction in alveolo-capillary surface area, potentially contributing to impaired gas exchange with increased risk for exercise intolerance, pulmonary hypertension, and poor tolerance of acute respiratory infections.

Pathogenesis of BPD

BPD represents the response of the lung to injury during a critical period of lung growth, that is, during the canalicular period (17 to 26 weeks in the human), a time during which airspace septation and vascular development increase dramatically. In some embodiments, factors that increase the susceptibility of the premature newborn to the development of BPD, include surfactant deficiency, decreased antioxidant defenses, impaired epithelial ion and water transport function, and lung structural immaturity. In some embodiments, lung injury after premature birth and the subsequent arrest of lung growth results from complex interactions between multiple adverse stimuli, including inflammation, hyperoxia, mechanical ventilation, and infection, of the poorly defended developing lung. In some embodiments, prenatal exposure to proinflammatory cytokines, such as TNF-α, IL-6, IL-8, and others, due to maternal chorioamnionitis, enhance lung maturation in utero, but increase the risk for BPD.

Hyperoxia and oxidant stress are critical factors in the development of BPD. In some embodiments, the transition of the premature newborn from the low-oxygen tension environment of the normal fetus to the relative hyperoxia of extrauterine life increases the risk for BPD with decreased alveolarization and a dysmorphic vasculature. In some embodiments, the premature change in the oxygen environment impedes normal epithelial-mesenchymal interactions and leads to alterations in endothelial cell survival, differentiation, and organization in the microvasculature. In some embodiments, a premature infant is especially susceptible to reactive oxidant species (ROS)-induced damage owing to the lack of adequate antioxidants after premature birth. In some embodiments, antioxidant enzymes [e.g., superoxide dismutase (SOD), catalase, and glutathione peroxidase] markedly increase during late gestation. In some additional embodiments, the ability to increase synthesis of antioxidant enzymes in response to hyperoxia is decreased in preterm animals, so premature birth may precede the normal up-regulation of antioxidants, which persists during early postnatal life. In some embodiments, endothelial and alveolar type II cells are extremely susceptible to hyperoxia and ROS-induced injury, leading to increased edema, cellular dysfunction, and impaired cell survival and growth.

In some embodiments, even in the absence of overt signs of baro- or volutrauma, treatment of premature neonates with mechanical ventilation initiates and promotes lung injury with inflammation and permeability edema, and contributes to BPD. In some embodiments, ventilator-associated lung injury (VALI) results from stretching distal airway epithelium and capillary endothelium, which increases permeability edema, inhibits surfactant function, and provokes a complex inflammatory cascade. In some embodiments, even brief periods of positive-pressure ventilation, such as during resuscitation in the delivery room, can cause bronchiolar epithelial and endothelial damage in the lung, setting the stage for progressive lung inflammation and injury.

Lung inflammation, whether induced prior to birth (from chorioamnionitis) or during the early postnatal period (due to hyperoxia or VALI) plays a prominent role in the development of BPD. In some embodiments, the risk for BPD is associated with sustained increases in tracheal fluid neutrophil counts, activated macrophages, high concentrations of lipid products, oxidant-inactivated α-1-antitrypsin activity, and proinflammatory cytokines, including IL-6 and IL-8, and decreased IL-10 levels. In some embodiments, release of early response cytokines, such as TNF-α, IL-1β, IL-8, and TGF-β, by macrophages and the presence of soluble adhesion molecules (i.e., selectins) may impact other cells to release chemoattractants that recruit neutrophils and amplify the inflammatory response. In some embodiments, elevated concentrations of proinflammatory cytokines in conjunction with reduced anti-inflammatory products (i.e., IL-10) appear in tracheal aspirates within a few hours of life in infants subsequently developing BPD. In some embodiments, increased elastase and collagenase release from activated neutrophils may directly destroy the elastin and collagen framework of the lung, and markers of collagen and elastin degradation can be recovered in the urine of infants with BPD. In some embodiments, infection from relatively low virulence organisms, such as airway colonization with Ureaplasma urealyticum, may augment the inflammatory response, further increasing to the risk for BPD. In some embodiments, other factors, such as nutritional deficits and genetic factors, such as vitamin A and E deficiency or single nucleotide polymorphism variants of the surfactant proteins, respectively, are likely to increase risk for BPD in some premature newborns.

Pulmonary Circulation in BPD

In addition to adverse effects on the airway and distal airspace, acute lung injury also impairs growth, structure, and function of the developing pulmonary circulation after premature birth. In some embodiments, endothelial cells are particularly susceptible to oxidant injury through hyperoxia or inflammation. In some embodiments, the media of small pulmonary arteries undergoes striking changes, including smooth muscle cell proliferation, precocious maturation of immature mesenchymal cells into mature smooth muscle cells, and incorporation of fibroblasts/myofibroblasts into the vessel wall. In some embodiments, structural changes in the lung vasculature contribute to high pulmonary vascular resistance (PVR) through narrowing of the vessel diameter and decreased vascular compliance. In some embodiments, in addition to these structural changes, the pulmonary circulation is further characterized by abnormal vasoreactivity, which also increases PVR. In some embodiments, decreased angiogenesis may limit vascular surface area, causing further elevations of PVR, especially in response to high cardiac output with exercise or stress.

Overall, early injury to the lung circulation leads to the rapid development of pulmonary hypertension, which contributes significantly to the morbidity and mortality of severe BPD. In some embodiments, high mortality rates occur in infants with BPD and pulmonary hypertension who require prolonged ventilator support. In some embodiments, pulmonary hypertension is a marker of more advanced BPD, and elevated PVR also causes poor right ventricular function, impaired cardiac output, limited oxygen delivery, increased pulmonary edema and, perhaps, a higher risk for sudden death. In some embodiments, physiologic abnormalities of the pulmonary circulation in BPD include elevated PVR and abnormal vasoreactivity, as evidenced by the marked vasoconstrictor response to acute hypoxia. In some embodiments, even mild hypoxia causes marked elevations in pulmonary artery pressure in infants with modest basal levels of pulmonary hypertension. In some embodiments, treatment levels of oxygen saturations above 92-94% effectively lower pulmonary artery pressure. In some embodiments, strategies to lower pulmonary artery pressure or limit injury to the pulmonary vasculature may limit the subsequent development of pulmonary hypertension in BPD.

Finally, pulmonary hypertension and right heart function remain major clinical concerns in infants with BPD. In some embodiments, pulmonary vascular disease in BPD also includes reduced pulmonary artery density owing to impaired growth, which contributes to physiologic abnormalities of impaired gas exchange, as well as to the actual pathogenesis of BPD. In some embodiments, impaired angiogenesis impedes alveolarization and strategies that preserve and enhance endothelial cell survival, growth, and function provide therapeutic approaches for the prevention of BPD.

Altered Signaling of Angiogenic Factors in BPD

Multiple growth factors and signaling systems play important roles in normal lung vascular growth. In some embodiments, premature delivery and changes in oxygen tension, inflammatory cytokines, and other signals alter normal growth factor expression and signaling and thus lung/lung vascular development. In some embodiments, the growth factor is VEGF. Impaired VEGF signaling has been associated with the pathogenesis of BPD in the clinical setting. In some embodiments, VEGF is found to be lower in tracheal fluid samples from premature neonates who subsequently develop BPD than those who do not develop chronic lung disease (185). In some embodiments, hyperoxia down-regulates lung VEGF expression, and pharmacologic inhibition of VEGF signaling impairs lung vascular growth and inhibits alveolarization. The biologic basis for impaired VEGF signaling leading to decreased vascular growth and impaired alveolarization is well established.

Vascular Growth and Alveolarization

As described above, close coordination of growth between airways and vessels is essential for normal lung development. In some embodiments, failure of pulmonary vascular growth during a critical period of lung growth (saccular or alveolar stages of development) decreases septation and ultimately contributes to the lung hypoplasia that characterizes BPD. In some embodiments, angiogenesis is involved in alveolarization during lung development and mechanisms that injure and inhibit lung vascular growth may impede alveolar growth after premature birth. In some embodiments, inhibition of lung vascular growth during a critical period of postnatal lung growth impairs alveolarization.

Flt-1 Receptor

Flt-1 receptor, also known as vascular endothelial growth factor receptor 1, is a receptor that is encoded by the FLT1 gene. The vascular endothelial growth factor (VEGF) family of signal glycoproteins act as potent promoters of angiogenesis during embryogenesis and postnatal growth. Specifically, the binding of the VEGF-A ligand with the VEGF receptors has been shown to promote vascular permeability and also trigger endothelial cell migration, proliferation, and survival, and the newly formed endothelial cells provide the basic structure of new vasculatures. The dominant VEGF signal molecule for angiogenesis, VEGF-A, mediates its signal through VEGF receptor-1 (VEGFR-1, also known as Flt-1) and VEGF receptor-2 (VEGFR-2, also known as Flk-1). A soluble form of Flt-1 (sFlt-1) also exists, but lacks an intracellular signaling domain and thus is believed to only serve in a regulatory capacity by sequestering VEGF-A or other ligands that bind to it. sFlt-1 and other molecules containing Flt-1 binding sites that are not linked to an intracellular signal transduction pathway are referred to as "decoy receptors". Flt-1 and Flk-1 receptors contain an extracellular VEGF-A-binding domain and an intracellular tyrosine kinase domain, and both show expression during the developmental stage and tissue regeneration in hemangioblasts and endothelial cell lineages. Flt-1 has about 10 times greater binding affinity for VEGF-A (Kd~2-10 pM) compared to Flk-1, but the weaker tyrosine kinase domain indicates that angiogenic signal transduction following VEGF-A binding to Flt-1 is comparably weaker than the Flk-1 signal. As such, homozygous Flt-1 gene knockout mice die in the embryonic stage from endothelial cell overproduction and blood vessel disorganization. Inversely, homozygous Flk-1 gene knockout mice die from defects in the development of organized blood vessels due to lack of yolk-sac blood island formation during embryogenesis. Both the Flt-1 and Flk-1 receptors are needed for normal development, but selective augmentation in VEGF-A concentration may allow for greater binding to the Flk-1 receptor and induce a pro-angiogenic effect that increases capillary density and facilitates reduction of fibrosis and inflammation, and mitigation of symptoms and features associated with BPD.

As used herein, the term "Flt-1 receptor" refers to both soluble and membrane associated Flt-1 receptors, or functional fragments thereof.

Anti-Flt-1 Antibodies

As used herein, the term "anti-Flt-1 antibodies" refers to any antibodies, or antigen-binding fragments thereof, that bind to a Flt-1 receptor (e.g., soluble or membrane associated Flt-1 receptor). In some embodiments, anti-Flt-1 antibodies are produced that bind with high affinity to Flt-1 receptors. Without wishing to be bound by theory, it is believed that anti-Flt-1 antibody binding to Flt-1 receptors inhibits one or more endogenous ligands from binding to Flt-1 and thereby allowing a greater amount of available ligand to associate with other VEGF receptors, such as the Flk-1 receptor. Increased activation of the Flk-1 receptor could increases capillary density and facilitates reduction of fibrosis and inflammation, and mitigation of symptoms and features associated with BPD. In some embodiments, antibody binding to Flt-1 receptors increases the amount of VEGF available to bind to other VEGF receptors.

In some embodiments the anti-Flt-1 antibody or antigen-binding fragment thereof comprises the sequences provided in Table 1.

TABLE 1

| Heavy Chain Variable Region | CDR1 | CDR2 | CDR3 |
| --- | --- | --- | --- |
| IGHV3-23*01 | SYAMS (SEQ ID NO: 1) | AISGSGGSTYYADSVKG (SEQ ID NO: 5) | ---------------DY (SEQ ID NO: 15) |
| IGHV3-23*04 | SYAMS (SEQ ID NO: 1) | AISGSGGSTYYADSVKG (SEQ ID NO: 5) | ---------------DY (SEQ ID NO: 15) |
| 13B4_VH | DYSMS (SEQ ID NO: 2) | AISWNGDSTYYAESMKG (SEQ ID NO: 6) | SWATPIESLYYYGMDY (SEQ ID NO: 16) |
| 27H4_VH (97.6_1.0 | DYSMS (SEQ ID NO: 2) | AISWNGDSTYYAESLKG (SEQ ID NO: 7) | SWATPIESLYYYGSDY (SEQ ID NO: 17) |
| 27H9_VH (97.5_1.1 | DYSMS (SEQ ID NO: 2) | AISWNGDSTYYAESAKG (SEQ ID NO: 8) | SWATPIESLYYYGSDY (SEQ ID NO: 17) |
| 25D4_VH (97.0_0.9 | DYSAS (SEQ ID NO: 3) | AISWNGDSTYYAESVKG (SEQ ID NO: 9) | SWATPIESLYYYGSDY (SEQ ID NO: 17) |
| 25G9_VH (97.0_0.9 | DYSMS (SEQ ID NO: 2) | AITWSGDSTYYAESVKG (SEQ ID NO: 10) | SWATPIESLYYYGTDY (SEQ ID NO: 18) |
| 25E11_VH (97.5_1. | DYSMS (SEQ ID NO: 2) | AISWNGDSTYYAESAKG (SEQ ID NO: 8) | SWATPIESLYYYGSDY (SEQ ID NO: 17) |
| 29E2_VH (96.3_1.1 | DYSLS (SEQ ID NO: 4) | AISWNGDSTYYAESVKG (SEQ ID NO: 9) | SWATPIESLYYYGSDY (SEQ ID NO: 17) |
| 27G9_VH (96.3_1.3 | DYSAS (SEQ ID NO: 3) | AISWSGDSTYYAESLKG (SEQ ID NO: 11) | SWATPIESLYYYGSDY (SEQ ID NO: 17) |
| 27H6_VH (97.5_ | DYSAS (SEQ ID NO: 3) | AISWSGDSTYYAESVKG (SEQ ID NO: 12) | SWATPIESLYYYGSDY (SEQ ID NO: 17) |
| 27H9_NG/QG | DYSMS (SEQ ID NO: 2) | AISWQGDSTYYAESAKG (SEQ ID NO: 13) | SWATPIESLYYYGSDY (SEQ ID NO: 17) |
| 27H9_NG/NA | DYSMS (SEQ ID NO: 2) | AISWNADSTYYAESAKG (SEQ ID NO: 14) | SWATPIESLYYYGSDY (SEQ ID NO: 17) |
| 27H9_NA_+_AAA | DYSMS (SEQ ID NO: 2) | AISWNADSTYYAESAKG (SEQ ID NO: 14) | SWATPIESLYYYGSDY (SEQ ID NO: 17) |
| Light Chain Variable Region | CDR1 | CDR2 | CDR3 |
| IGLV3-9*01 | GGNNIGSKNVH (SEQ ID NO: 19) | RDSNRPS (SEQ ID NO: 22) | QV-------VV (SEQ ID NO: 25) |

TABLE 1-continued

| | | | |
|---|---|---|---|
| IGLV3-9*02 | GGNNLGYKSVH (SEQ ID NO: 20) | RDNNRPS (SEQ ID NO: 23) | QV-------VV (SEQ ID NO: 25) |
| LC_21B3 | GGNNIGSQTAQ (SEQ ID NO: 21) | ANNRRPS (SEQ ID NO: 24) | QVWDGSTQAIV (SEQ ID NO: 26) |
| VL_27H4 | GGNNIGSQTAQ (SEQ ID NO: 21) | ANNRRPS (SEQ ID NO: 24) | QVWEDSTQAIV (SEQ ID NO: 27) |
| VL_27H9 | GGNNIGSQTAQ (SEQ ID NO: 21) | ANNRRPS (SEQ ID NO: 24) | QVWDESTQAIV (SEQ ID NO: 28) |
| VL_25D4 | GGNNIGSQTAQ (SEQ ID NO: 21) | ANNRRPS (SEQ ID NO: 24) | QVWAASTQAIV (SEQ ID NO: 29) |
| VL_25G9 | GGNNIGSQTAQ (SEQ ID NO: 21) | ANNRRPS (SEQ ID NO: 24) | QVWDDSTQAIV (SEQ ID NO: 30) |
| VL_25E11 | GGNNIGSQTAQ (SEQ ID NO: 21) | ANNRRPS (SEQ ID NO: 24) | QVWEASTQAIV (SEQ ID NO: 31) |
| VL_29E2 | GGNNIGSQTAQ (SEQ ID NO: 21) | ANNRRPS (SEQ ID NO: 24) | QVWDASTQAIV (SEQ ID NO: 32) |
| VL_27G9 | GGNNIGSQTAQ (SEQ ID NO: 21) | ANNRRPS (SEQ ID NO: 24) | QVWEESTQAIV (SEQ ID NO: 33) |
| VL_27H6 | GGNNIGSQTAQ (SEQ ID NO: 21) | ANNRRPS (SEQ ID NO: 24) | QVWDGSTQAIV (SEQ ID NO: 26) |
| VL_27H6(DA) | GGNNIGSQTAQ (SEQ ID NO: 21) | ANNRRPS (SEQ ID NO: 24) | QVWDASTQAIV (SEQ ID NO: 32) |
| VL_27H6(EG) | GGNNIGSQTAQ (SEQ ID NO: 21) | ANNRRPS (SEQ ID NO: 24) | QVWEGSTQAIV (SEQ ID NO: 34) |

| Heavy Chain Variable Region | VH |
|---|---|
| IGHV3-23*01 | EVQLLESGGGLVQPGGSLRLSCAASGFTFS SYAMS WVRQAPGKGLEWVS AISGSGGSTYYADSVKGRFTISRDNSKNTLYLQMNSLRAEDTAVYYCAK ---------------DY WGQGTLVTVSS (SEQ ID NO: 35) |
| IGHV3-23*04 | EVQLVESGGGLVQPGGSLRLSCAASGFTFS SYAMS WVRQAPGKGLEWVS AISGSGGSTYYADSVKG RFTISRDNSKNTLYLQMNSLRAEDTAVYYCAK ---------------DY WGQGTLVTVSS (SEQ ID NO: 36) |
| 13B4_VH | ELQLVESGGGLVQPGGSLRLSCAASGFTFR DYSMS WVRQAPGKGLEWVS AISWNGDSTYYAESMKG RFTISRDNAKNTLYLQMNSLKSEDTAVYYCAK SWATPIESLYYYGMDY WGKGTLVTVSS (SEQ ID NO: 37) |
| 27H4_VH (97.6_1.0) | ELQLVESGGGLVQPGGSLRLSCAASGFTFR DYSMS WVRQAPGKGLEWVS AISWNGDSTYYAESLKG RFTISRDNAKNTLYLQMNSLRAEDTAVYYCAK SWATPIESLYYYGSDY WGQGTLVTVSS (SEQ ID NO: 38) |
| 27H9_VH (97.5_1.1) | EVQLLESGGGLVQPGGSLRLSCAASGFTFR DYSMS WVRQAPGKGLEWVS AISWNGDSTYYAESAKG RFTISRDNSKNTLYLQMNSLRAEDTAVYYCAK SWATPIESLYYYGSDY WGQGTLVTVSS (SEQ ID NO: 39) |
| 25D4_VH (97.0_0.9) | EVQLLESGGGLVQPGGSLRLSCAASGFTFR DYSAS WVRQAPGKGLEWVS AISWNGDSTYYAESVKG RFTISRDNAKNTLYLQMNSLRAEDTAVYYCAK SWATPIESLYYYGSDY WGQGTLVTVSS (SEQ ID NO: 40) |
| 25G9_VH (97.0_0.9) | EVQLLESGGGLVQPGGSLRLSCAASGFTFR DYSMS WVRQAPGKGLEWVS AITWSGDSTYYAESVKG RFTISRDNSKNTLYLQMNSLRAEDTAVYYCAK SWATPIESLYYYGTDY WGKGTLVTVSS (SEQ ID NO: 41) |
| 25E11_VH (97.5_1.) | EVQLLESGGGLVQPGGSLRLSCAASGFTFR DYSMS WVRQAPGKGLEWVS AISWNGDSTYYAESAKG RFTISRDNSKNTLYLQMNSLRAEDTAVYYCAK SWATPIESLYYYGSDY WGQGTLVTVSS (SEQ ID NO: 42) |

TABLE 1-continued

| | |
|---|---|
| 29E2 VH (96.3_ 1.1 | EVQLVESGGGLVQPGGSLRLSCAASGFTFR DYSLS WVRQAPGKGLEWVS AISWNGDSTYYAESVKG RFTISRDNSKNTLYLQMNSLRAEDTAVYYCAK SWATPIESLYYYGSDY WGKGTLVTVSS (SEQ ID NO: 43) |
| 27G9 VH (96.3_ 1.3 | EVQLLESGGGLVQPGGSLRLSCAASGFTFR DYSAS WVRQAPGKGLEWVS AISWSGDSTYYAESLKG RFTISRDNSKNTLYLQMNSLRAEDTAVYYCAK SWATPIESLYYYGSDY WGKGTLVTVSS (SEQ ID NO: 44) |
| 27H6 VH (97.5_ | ELQLVESGGGLVQPGGSLRLSCAASGFTFS DYSAS WVRQAPGKGLEWVS AISWSGDSTYYAESVKG RFTIFRDNSKNTLYLQMNSLRAEDTAVYYCAK SWATPIESLYYYGSDY WGQGTLVTVSS (SEQ ID NO: 45) |
| 27H9_NG/QG | EVQLLESGGGLVQPGGSLRLSCAASGFTFR DYSMS WVRQAPGKGLEWVS AISWQGDSTYYAESAKG RFTISRDNSKNTLYLQMNSLRAEDTAVYYCAK SWATPIESLYYYGSDY WGQGTLVTVSS (SEQ ID NO: 46) |
| 27H9_NG/NA | EVQLLESGGGLVQPGGSLRLSCAASGFTFR DYSMS WVRQAPGKGLEWVS AISWNADSTYYAESAKG RFTISRDNSKNTLYLQMNSLRAEDTAVYYCAK SWATPIESLYYYGSDY WGQGTLVTVSS (SEQ ID NO: 47) |
| 27H9_NA_+_AAA | EVQLLESGGGLVQPGGSLRLSCAASGFTFR DYSMS WVRQAPGKGLEWVS AISWNADSTYYAESAKG RFTISRDNSKNTLYLQMNSLRAEDTAVYYCAK SWATPIESLYYYGSDY WGQGTLVTVSS (SEQ ID NO: 48) |
| Light Chain Variable Region | VL |
| IGLV3-9*01 | SYELTQPLSVSVALGQTARITC GGNNIGSKNVH WYQQKPGQAPVLVIY RDSNRPS GIPERFSGSNSGNTATLTISRAQAGDEADYYC QV-------VV FGGGTKLTVL (SEQ ID NO: 49) |
| IGLV3-9*02 | SYELTQPLSVSVALGQAARITC GGNNLGYKSVH WYQQKPGQAPVLVIY RDNNRPS GIPERFSGSNSGNTATLTISRAQAGDEADYYC QV-------VV FGGGTKLTVL (SEQ ID NO: 50) |
| LC_21B3 | SYELTQSPSVSVALRQTAKITC GGNNIGSQTAQ WYQQKPGQAPVLVIY ANNRRPS GIPERFSGSKSGNTATLTISGAQAEDEADYYC QVWDGSTQAIV FGGGTHLTVL (SEQ ID NO: 51) |
| VL_27H4 | SYELTQPLSVSVALGQTARITC GGNNIGSQTAQ WYQQKPGQAPVLVIY ANNRRPS GIPERFSGSKSGNTATLTISRAQAEDEADYYC QVWEDSTQAIV FGGGTKLTVL (SEQ ID NO: 52) |
| VL_27H9 | SYELTQPLSVSVALRQTARITC GGNNIGSQTAQ WYQQKPGQAPVLVIY ANNRRPS GIPERFSGSKSGNTATLTISRAQAEDEADYYC QVWDESTQAIV FGGGTKLTVL (SEQ ID NO: 53) |
| VL_25D4 | SYELTQPLSVSVALGQTARITC GGNNIGSQTAQ WYQQKPGQAPVLVIY ANNRRPS GIPERFSGSKSGNTATLTISGAQAEDEADYYC QVWAASTQAIV FGGGTKLTVL (SEQ ID NO: 54) |
| VL_25G9 | SYELTQPLSVSVALRQAARITC GGNNIGSQTAQ WYQQKPGQAPVLVIY ANNRRPS GIPERFSGSKSGNTATLTISRAQAEDEADYYC QVWDDSTQAIV FGGGTKLTVL (SEQ ID NO: 55) |
| VL_25E11 | SYELTQPLSVSVALRQAARITC GGNNIGSQTAQ WYQQKPGQAPVLVIY ANNRRPS GIPERFSGSKSGNTATLTISRAQAEDEADYYC QVWEASTQAIV FGGGTKLTVL (SEQ ID NO: 56) |
| VL_29E2 | SYELTQSPSVSVALRQTAKITC GGNNIGSQTAQ WYQQKPGQAPVLVIY ANNRRPS GIPERFSGSKSGNTATLTISGAQAGDEADYYC QVWDASTQAIV FGGGTKLTVL (SEQ ID NO: 57) |

TABLE 1-continued

| | |
|---|---|
| VL_27G9 | SYELTQPLSVSVALGQTAKITC GGNNIGSQTAQ WYQQKPGQAPVLVIY ANNRRPS GIPERFSGSKSGNTATLTISRAQAEDEADYYC QVWEESTQAIV FGGGTHLTVL<br>(SEQ ID NO: 58) |
| VL_27H6 | SYELTQPLSVSVALRQAAKITC GGNNIGSQTAQ WYQQKPGQAPVLVIY ANNRRPS GIPERFSGSKSGNTATLTISRAQAGDEADYYC QVWDGSTQAIV FGGGTKLTVL<br>(SEQ ID NO: 59) |
| VL_27H6(DA) | SYELTQPLSVSVALRQAAKITC GGNNIGSQTAQ WYQQKPGQAPVLVIY ANNRRPS GIPERFSGSKSGNTATLTISRAQAGDEADYYC QVWDASTQAIV FGGGTKLTVL<br>(SEQ ID NO: 60) |
| VL_27H6(EG) | SYELTQPLSVSVALRQAAKITC GGNNIGSQTAQ WYQQKPGQAPVLVIY ANNRRPS GIPERFSGSKSGNTATLTISRAQAGDEADYYC QVWEGSTQAIV FGGGTKLTVL<br>(SEQ ID NO: 61) |
| Heavy Chain | Heavy Chain Sequence (VH + CH1/2/3) |
| VH_27H6_DG/EG | ELQLVESGGGLVQPGGSLRLSCAASGFTFSDYSASWVRQAPGKGLEWVSAISWS GDSTYYAESVKGRFTIFRDNSKNTLYLQMNSLRAEDTAVYYCAKSWATPIESLY YYGSDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFS CSVMHEALHNHYTQKSLSLSPGK<br>(SEQ ID NO: 62) |
| VH_27H6_DG/DA | ELQLVESGGGLVQPGGSLRLSCAASGFTFSDYSASWVRQAPGKGLEWVSAISWS GDSTYYAESVKGRFTIFRDNSKNTLYLQMNSLRAEDTAVYYCAKSWATPIESLY YYGSDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFS CSVMHEALHNHYTQKSLSLSPGK<br>(SEQ ID NO: 63) |
| VH_27H9_NG/QG | EVQLLESGGGLVQPGGSLRLSCAASGFTFRDYSMSWVRQAPGKGLEWVSAISWQ GDSTYYAESAKGRFTISRDNSKNTLYLQMNSLRAEDTAVYYCAKSWATPIESLY YYGSDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFS CSVMHEALHNHYTQKSLSLSPGK<br>(SEQ ID NO: 64) |
| VH_27H9_NG/NA | EVQLLESGGGLVQPGGSLRLSCAASGFTFRDYSMSWVRQAPGKGLEWVSAISWN ADSTYYAESAKGRFTISRDNSKNTLYLQMNSLRAEDTAVYYCAKSWATPIESLY YYGSDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFS CSVMHEALHNHYTQKSLSLSPGK<br>(SEQ ID NO: 65) |
| VH_27H4_NG/QG | ELQLVESGGGLVQPGGSLRLSCAASGFTFRDYSMSWVRQAPGKGLEWVSAISWQ GDSTYYAESLKGRFTISRDNAKNTLYLQMNSLRAEDTAVYYCAKSWATPIESLY YYGSDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFS CSVMHEALHNHYTQKSLSLSPGK<br>(SEQ ID NO: 66) |
| VH_27H4_NG/NA | ELQLVESGGGLVQPGGSLRLSCAASGFTFRDYSMSWVRQAPGKGLEWVSAISWN ADSTYYAESLKGRFTISRDNAKNTLYLQMNSLRAEDTAVYYCAKSWATPIESLY |

TABLE 1-continued

| | |
|---|---|
| | YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 67) |
| VH_27H4_NA_+_<br>AAA | ELQLVESGGGLVQPGGSLRLSCAASGFTFRDYSMSWVRQAPGKGLEWVSAISWN<br>ADSTYYAESLKGRFTISRDNAKNTLYLQMNSLRAEDTAVYYCAKSWATPIESLY<br>YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPEAAGAPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 68) |
| VH_27H9_NA_+_<br>AAA | EVQLLESGGGLVQPGGSLRLSCAASGFTFRDYSMSWVRQAPGKGLEWVSAISWN<br>ADSTYYAESAKGRFTISRDNSKNTLYLQMNSLRAEDTAVYYCAKSWATPIESLY<br>YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPEAAGAPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 69) |
| VH_21B3_AAA | ELQLVESGGGLVQPGGSLRLSCAASGFTFRDYSMSWVRQAPGKGLEWVSAISWN<br>GDSTYYAESMKGRFTISRDNAKNTLYLQMNSLKSEDTAVYYCAKSWATPIESLY<br>YYGMDYWGKGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPEAAGAPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 70) |
| VH_27H6 | ELQLVESGGGLVQPGGSLRLSCAASGFTFSDYSASWVRQAPGKGLEWVSAISWS<br>GDSTYYAESVKGRFTIFRDNSKNTLYLQMNSLRAEDTAVYYCAKSWATPIESLY<br>YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 71) |
| VH_27H4 | ELQLVESGGGLVQPGGSLRLSCAASGFTFRDYSMSWVRQAPGKGLEWVSAISWN<br>GDSTYYAESLKGRFTISRDNAKNTLYLQMNSLRAEDTAVYYCAKSWATPIESLY<br>YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 72) |
| VH_27H9 | EVQLLESGGGLVQPGGSLRLSCAASGFTFRDYSMSWVRQAPGKGLEWVSAISWN<br>GDSTYYAESAKGRFTISRDNSKNTLYLQMNSLRAEDTAVYYCAKSWATPIESLY<br>YYGSDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMHEALHNHYTQKSLSLSPGK<br>(SEQ ID NO: 73) |
| HC_13B4 | ELQLVESGGGLVQPGGSLRLSCAASGFTFRDYSMSWVRQAPGKGLEWVSAISWN<br>GDSTYYAESMKGRFTISRDNAKNTLYLQMNSLKSEDTAVYYCAKSWATPIESLY<br>YYGMDYWGKGTLVTVSSASTKGPSVFPLAPSSKSTSGGTAALGCLVKSYFPEPV<br>TVSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTCV |

TABLE 1-continued

| | |
|---|---|
| | VVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFS<br>CSVMNEALHNHYTQKSLSLSPGK<br>(SEQ ID NO: 74) |
| Light Chain | Light Chain Sequence (VL + CL) |
| LC_27H6_DG/EG | SYELTQPLSVSVALRQAAKITCGGNNIGSQTAQWYQQKPGQAPVLVIYANNRRP<br>SGIPERFSGSKSGNTATLTISRAQAGDEADYYCQVWEGSTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 75) |
| LC_27H6_DG/DA | SYELTQPLSVSVALRQAAKITCGGNNIGSQTAQWYQQKPGQAPVLVIYANNRRP<br>SGIPERFSGSKSGNTATLTISRAQAGDEADYYCQVWDASTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 76) |
| LC_27H9_NG/QG | SYELTQPLSVSVALRQTARITCGGNNIGSQTAQWYQQKPGQAPVLVIYANNRRP<br>SGIPERFSGSKSGNTATLTISRAQAEDEADYYCQVWDESTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 77) |
| LC_27H9_NG/NA | SYELTQPLSVSVALRQTARITCGGNNIGSQTAQWYQQKPGQAPVLVIYANNRRP<br>SGIPERFSGSKSGNTATLTISRAQAEDEADYYCQVWDESTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 78) |
| LC_27H4_NG/QG | SYELTQPLSVSVALGQTARITCGGNNIGSQTAQWYQQKPGQAPVLVIYANNRRP<br>SGIPERFSGSKSGNTATLTISRAQAEDEADYYCQVWEDSTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 79) |
| LC_27H4_NG/NA | SYELTQPLSVSVALGQTARITCGGNNIGSQTAQWYQQKPGQAPVLVIYANNRRP<br>SGIPERFSGSKSGNTATLTISRAQAEDEADYYCQVWEDSTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 80) |
| LC_27H4_NA_+_AAA | SYELTQPLSVSVALGQTARITCGGNNIGSQTAQWYQQKPGQAPVLVIYANNRRP<br>SGIPERFSGSKSGNTATLTISRAQAEDEADYYCQVWEDSTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 81) |
| LC_27H9_NA_+_AAA | SYELTQPLSVSVALRQTARITCGGNNIGSQTAQWYQQKPGQAPVLVIYANNRRP<br>SGIPERFSGSKSGNTATLTISRAQAEDEADYYCQVWDESTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 82) |
| LC_21B3_AAA | SYELTQSPSVSVALRQTAKITCGGNNIGSQTAQWYQQKPGQAPVLVIYANNRRP<br>SGIPERFSGSKSGNTATLTISGAQAEDEADYYCQVWDGSTQAIVEGGGTKLTVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 83) |
| LC_27H6 | SYELTQPLSVSVALRQAAKITCGGNNIGSQTAQWYQQKPGQAPVLVIYANNRRP<br>SGIPERFSGSKSGNTAILTISRAQAGDEADYYCQVWDGSTQAIVEGGGIKLIVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 84) |
| LC_27H4 | SYELTQPLSVSVALGQTARITCGGNNIGSQTAQWYQQKPGQAPVLVIYANNRRP<br>SGIPERFSGSKSGNTAILTISRAQAEDEADYYCQVWEDSTQAIVEGGGIKLIVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 85) |
| LC_27H9 | SYELTQPLSVSVALRQTARITCGGNNIGSQTAQWYQQKPGQAPVLVIYANNRRP<br>SGIPERFSGSKSGNTAILTISRAQAEDEADYYCQVWDESTQAIVEGGGIKLIVL<br>GQPKAAPSVTLFPPSSEELQANKATLVCLISDFYPGAVTVAWKADSSPVKAGVE<br>TTTPSKQSNNKYAASSYLSLTPEQWKSHRSYSCQVTHEGSTVEKTVAPTECS<br>(SEQ ID NO: 86) |

TABLE 1-continued

| Constant Region | CH1-CH2-CH3 |
| --- | --- |
| 27H6_DG/EG | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSL<br>SLSPGK (SEQ ID NO: 87) |
| 27H6_DG/DA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSL<br>SLSPGK (SEQ ID NO: 87) |
| 27H9_NG/QG | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK (SEQ ID NO: 87) |
| 27H9_NG/NA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 27H4_NG/QG | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 27H4_NG/NA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 27H4_NA_+_AAA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 88) |
| 27H9_NA_+_AAA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 88) |
| 21B3_AAA | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 88) |

TABLE 1-continued

| | |
|---|---|
| 27H6 | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 27H4 | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 27H9 | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMHEALHNHYTQKSL<br>SLSPGK<br>(SEQ ID NO: 87) |
| 13B4 | ASTKGPSVFPLAPSSKSTSGGTAALGCLVKSYFPEPVTVSWNSGALTSGVHTFP<br>AVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSRDELTKNQVSLICLVKGFYPSDIAVEWESNGQP<br>ENNYKTTPPVLDSDGSFFLYSKLTVDKSRWQQGNVFSCSVMNEALHNHYTQKSL<br>SLSPGK<br>(SEQ ID NO: 89) |

In some embodiments, the anti-Flt-1 antibody, or antigen-binding fragment thereof, comprises one or more complementarity determining regions (CDR) selected from the group consisting of a VL CDR1 defined by an amino acid sequence having at least 60%, 70%, 80%, 90%, 95% or 98% identity to any one of SEQ ID NO:19 to SEQ ID NO:21, a VL CDR2 defined by an amino acid sequence having at least 60%, 70%, 80%, 90%, 95% or 98% identity to any one of SEQ ID NO:22 to SEQ ID NO:24, a VL CDR3 defined by an amino acid sequence having at least 60%, 70%, 80%, 90%, 95% or 98% identity to any one of SEQ ID NO:25 to SEQ ID NO:34, a VH chain CDR1 defined by an amino acid sequence having at least 60%, 70%, 80%, 90%, 95% or 98% identity to any one of SEQ ID NO:1 to SEQ ID NO:4, a VH CDR2 defined by an amino acid sequence having at least 60%, 70%, 80%, 90%, 95% or 98% identity to any one of SEQ ID NO:5 to SEQ ID NO:14, and a VH CDR3 defined by an amino acid sequence having at least 60%, 70%, 80%, 90%, 95% or 98% identity to any one of SEQ ID NO:15 to SEQ ID NO:18. In some embodiments, the VH CDR3 is not SEQ ID NO:15. In some embodiments, the VL CDR3 is not SEQ ID NO:25.

In some embodiments, the one or more CDRs comprise the VL CDR3 defined by the amino acid sequence having at least 60%, 70%, 80%, 90%, 95% or 98% identity to any one of SEQ ID NO:25 to SEQ ID NO:34; and the VH CDR3 defined by the amino acid sequence having at least 60%, 70%, 80%, 90%, 95% or 98% identity to any one of SEQ ID NO:15 to SEQ ID NO:18. In some embodiments, the VH CDR3 is not SEQ ID NO:15. In some embodiments, the VL CDR3 is not SEQ ID NO:25.

In some embodiments, the one or more CDRs comprise the VL CDR1 defined by the amino acid sequence having at least 60%, 70%, 80%, 90%, 95% or 98% identity to any one of SEQ ID NO:19 to SEQ ID NO:21, the VL CDR2 defined by the amino acid sequence having at least 60%, 70%, 80%, 90%, 95% or 98% identity to any one of SEQ ID NO:22 to SEQ ID NO:24, and the VL CDR3 defined by amino acid sequence having at least 60%, 70%, 80%, 90%, 95% or 98% identity to any one of SEQ ID NO:25 to SEQ ID NO:34. In some embodiments, the VL CDR3 is not SEQ ID NO:25.

In some embodiments, the one or more CDRs comprise the VH CDR1 defined by the amino acid sequence having at least 60%, 70%, 80%, 90%, 95% or 98% identity to any one of SEQ ID NO:1 to SEQ ID NO:4, the VH CDR2 defined by the amino acid sequence having at least 60%, 70%, 80%, 90%, 95% or 98% identity to any one of SEQ ID NO:5 to SEQ ID NO:14, and the VH CDR3 defined by the amino acid sequence having at least 60%, 70%, 80%, 90%, 95% or 98% identity to any one of SEQ ID NO:15 to SEQ ID NO:18. In some embodiments, the VH CDR3 is not SEQ ID NO:15.

In some embodiments, the anti-Flt-1 antibody, or antigen-binding fragment thereof, comprises a VL chain comprising the VL CDR1, VL CDR2, and VL CDR3 defined by the amino acid sequence of SEQ ID NO:19, SEQ ID NO:22, and SEQ ID NO:25, respectively. In another embodiment, the anti-Flt-1 antibody, or antigen-binding fragment thereof, comprises a VL chain comprising the VL CDR1, VL CDR2, and VL CDR3 defined by the amino acid sequence of SEQ ID NO:20, SEQ ID NO:23, and SEQ ID NO:25, respectively. In yet another embodiment the anti-Flt-1 antibody, or antigen-binding fragment thereof, comprises a VL chain comprising the VL CDR1 and VL CDR2 defined by the amino acid sequence of SEQ ID NO:21, SEQ ID NO:24, respectively, and the VL CDR3 defined by the amino acid sequence of SEQ ID NO:26, SEQ ID NO:27, SEQ ID NO:28, SEQ ID NO:29, SEQ ID NO:30, SEQ ID NO:31, SEQ ID NO:32, SEQ ID NO:33 or SEQ ID NO:34. In a particular embodiment, the anti-Flt-1 antibody, or antigen-binding fragment thereof, comprises a VL chain comprising the VL CDR1 defined by the amino acid sequence of SEQ ID NO:21, the VL CDR2 defined by the amino acid sequence of SEQ ID NO:24, and the VL CDR3 defined by the amino acid sequence of SEQ ID NO:32. In some embodiments, the VL CDR3 is not SEQ ID NO:25.

In another embodiment, the anti-Flt-1 antibody, or antigen-binding fragment thereof, comprises a VH chain comprising the VH CDR1, VH CDR2, and VH CDR3 defined by the amino acid sequences of SEQ ID NO:1, SEQ ID NO:5, and SEQ ID NO:15, respectively. In another embodiment, the anti-Flt-1 antibody, or antigen-binding fragment thereof, comprises a VH chain comprising a VH CDR1, VH CDR2, and VH CDR3 defined by the amino acid sequences of SEQ ID NO:2, SEQ ID NO:6, and SEQ ID NO:16, respectively. In another embodiment, the anti-Flt-1 antibody or antigen-binding fragment thereof, comprises a VH chain comprising a VH CDR1, VH CDR2, and VH CDR3 defined by the amino acid sequences of SEQ ID NO:2, SEQ ID NO:10, and SEQ ID NO:18, respectively. In another embodiment, the anti-Flt-1 antibody, or antigen-binding fragment thereof, comprises a VH chain comprising the VH CDR1 and the VH CDR3 defined by the amino acid sequences of SEQ ID NO:2 and SEQ ID NO:17, respectively, and the VH CDR2 defined by the amino acid sequence of SEQ ID NO:7, SEQ ID NO:8, SEQ ID NO:13 or SEQ ID NO:14. In another embodiment, the anti-Flt-1 antibody, or antigen-binding fragment thereof, comprises a VH chain comprising the VH CDR1 and the VH CDR3 defined by the amino acid sequences of SEQ ID NO:3 and SEQ ID NO:17, respectively, and a VH CDR2 defined by the amino acid sequence of SEQ ID NO:9, SEQ ID NO:11 or SEQ ID NO:12. In another embodiment, the anti-Flt-1 antibody, or antigen-binding fragment thereof, comprises a VH chain comprising the VH CDR1, VH CDR2, and VH CDR3 defined by the amino acid sequences of SEQ ID NO:4, SEQ ID NO:9, and SEQ ID NO:17, respectively. In a particular embodiment, the anti-Flt-1 antibody, or antigen-binding fragment thereof, comprises a VH chain comprising the VH CDR1 defined by the amino acid sequence of SEQ ID NO:3, the VH CDR2 defined by the amino acid sequence of SEQ ID NO:12 and the VH CDR3 defined by the amino acid sequence of SEQ ID NO:17. In some embodiments, the VH CDR3 is not SEQ ID NO:15.

In another embodiment, the anti-Flt-1 antibody, or antigen-binding fragment thereof, comprises a light chain VL region comprising an amino acid sequence having at least 60%, 70%, 80%, 90%, 95% or 98% identity to any one of SEQ ID NO:49 to SEQ ID NO:61, and/or a heavy chain VH region comprising an amino acid sequence having at least 60%, 70%, 80%, 90%, 95% or 98% identity to any one of SEQ ID NO:35 to SEQ ID NO:48. In a particular embodiment, the VL region comprises the amino acid sequence of SEQ ID NO:60 and the VH region comprises the amino acid sequence of SEQ ID NO:45. In another embodiment, the antibody further comprises a heavy chain constant region comprising an amino acid sequence having at least 60%, 70%, 80%, 90%, 95% or 98% identity to any one of SEQ ID NO:87 to SEQ ID NO:89. In some embodiments, the light chain VL region is not SEQ ID NO:49. In some embodiments, the heavy chain VH region is not SEQ ID NO:35.

In another embodiment, the anti-Flt-1 antibody, or antigen-binding fragment thereof, comprises a light chain comprising an amino acid sequence having at least 60%, 70%, 80%, 90%, 95% or 98% identity to any one of SEQ ID NO:75 to SEQ ID NO:86, and/or a heavy chain comprising an amino acid sequence having at least 60%, 70%, 80%, 90%, 95% or 98% identity to any one of SEQ ID NO:62 to SEQ ID NO:74. In a particular embodiment, the light chain comprises the amino acid sequence of SEQ ID NO:76 and the heavy chain region comprises the amino acid sequence of SEQ ID NO:71.

In some embodiments, the heavy chain of the anti-Flt-1 antibody, or antigen-binding fragment thereof, comprises the amino acid sequence

```
                                    (SEQ ID NO: 108)
MGWSCIILFLVATATGVHSELQLVESGGGLVQPGGSLRLSCAASGFTFS

DYSASWVRQAPGKGLEWVSAISWSGDSTYYAESVKGRFTIFRDNSKNTL

YLQMNSLRAEDTAVYYCAKSWATPIESLYYYGSDYWGQGTLVTVSSAST

KGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPK

SCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGKX.
```

In some embodiments, the heavy chain of the anti-Flt-1 antibody, or antigen-binding fragment thereof, comprises the amino acid sequence

```
                                    (SEQ ID NO: 109)
ELQLVESGGGLVQPGGSLRLSCAASGFTFSDYSASWVRQAPGKGLEWVS

AISWSGDSTYYAESVKGRFTIFRDNSKNTLYLQMNSLRAEDTAVYYCAK

SWATPIESLYYYGSDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGK.
```

In some embodiments, the light chain of the anti-Flt-1 antibody, or antigen-binding fragment thereof, comprises the amino acid sequence

```
                                    (SEQ ID NO: 110)
MGWSCIILFLVATATGVHSSYELTQPLSVSVALRQAAKITCGGNNIGSQ

TAQWYQQKPGQAPVLVIYANNRRPSGIPERFSGSKSGNTATLTISRAQA

GDEADYYCQVWDASTQAIVFGGGTKLTVLGQPKAAPSVTLFPPSSEELQ

ANKATLVCLISDFYPGAVTVAWKADSSPVKAGVETTTPSKQSNNKYAAS

SYLSLTPEQWKSHRSYSCQVTHEGSTVEKTVAPTECSX.
```

In some embodiments, the anti-Flt-1 antibody, or antigen-binding fragment thereof, comprises a heavy chain of SEQ ID NO:108 or SEQ ID NO:109 and a light chain of SEQ ID NO:110 or SEQ ID NO:76.

In some embodiments, an anti-Flt-1 antibody, or antigen-binding fragment thereof, binds human Flt-1 with an affinity greater than about $10^{-7}$M, greater than about $0.5\times10^{-7}$, greater than about $10^{-8}$, greater than about $0.5\times10^{-8}$, greater than about $10^{-9}$M, greater than about $0.5\times10^{-9}$, greater than about $10^{-10}$M, greater than about $0.5\times10^{-10}$M, greater than about $10^{-11}$M, greater than about $0.5\times10^{-11}$M, greater than about $10^{-12}$M, or greater than about $0.5\times10^{-12}$M. In other embodiments, an anti-Flt-1 antibody, or antigen-binding fragment thereof, binds to mouse Flt-1 with an affinity greater than about $10^{-7}$M, greater than about $0.5\times10^{-7}$, greater than about $10^{-8}$, greater than about $0.5\times10^{-8}$, greater than about $10^{-9}$M, greater than about $0.5\times10^{-9}$, greater than about $10^{-10}$M, greater than about $0.5\times10^{-10}$M, greater than about $10^{-11}$M, greater than about $0.5\times10^{-11}$M, greater than about $10^{-12}$M, or greater than about $0.5\times10^{-12}$M. The affinity of an Flt-1 antibody may be measured, for example, in a surface plasmon resonance assay, such as a BIACORE assay.

In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM in a competition assay with human Flt-1. In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM in a competition assay with mouse Flt-1.

In some embodiments, an anti-Flt-1 antibody, or antigen-binding fragment thereof inhibits the binding and/or activity of VEGF at the Flt-1 receptor. In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM for inhibition of binding of VEGF to human Flt-1 in a competition assay.

In some embodiments, an anti-Flt-1 antibody, or antigen-binding fragment thereof completes with, and or inhibits VEGF binding to soluble Flt-1. In other embodiments, the competition, and or inhibition, is in a dose dependent manner. In particular embodiments, the inhibition of binding of VEGF to Flt-1 results in increased phosphorylation of VEGF R2. Without intending to be bound by theory, binding of the anti-Flt-1 antibody, or antigen-binding fragment thereof to Flt-1 inhibits the binding of VEGF to Flt-1. Unbound VEGF binds VEGF R2 which may be demonstrated by measuring phosphorylation of VEGF R2. In particular embodiments, the anti-Flt-1 antibody, or antigen-binding fragment rescues VEGF R2 phosphorylation in a dose dependent manner. For example, VEGF R2 phosphorylation may be rescued by at least about 100%, about 95%, about 90%, about 85%, about 80%, about 75%, about 70%, about 65%, about 60%, about 55%, about 50%, about 45%, about 40%, about 35% about 30%, about 25%, about 20%, about 15%, about 10% or about 5%.

In some embodiments, an anti-Flt-1 antibody, or antigen-binding fragment thereof provide greater than about 95%, greater than about 90%, greater than about 85%, greater than about 80%, greater than about 75%, greater than about 70%, greater than about 65%, greater than about 60%, greater than about 55%, greater than about 50%, greater than about 45%, greater than about 40%, greater than about 35%, greater than about 30%, greater than about 25%, greater than about 20%, greater than about 15%, or greater than about 10% rescue in a bioassay. In a particular embodiment the bioassay comprises human primary vein endothelial cells (HUVECs) stimulated with VEGF in the presence of sFlt-1 and an anti-Flt-1 antibody or antigen-binding fragment thereof. VEGF induced activation of cells may be assayed by determining the phosphorylation status of the VEGF R2 receptor. Data may be expressed as a percent rescue of the phosphorylation of the VEGF R2 receptor relative to the phosphorylation of the VEGF R2 receptor in the presence of sFlt-1 alone (e.g., without anti-Flt-1 antibodies).

In some embodiments, an anti-Flt-1 antibody, or antigen-binding fragment thereof, has a half-life of greater than about 200 hours, greater than about 150 hours, greater than about 100 hours, greater than about 95 hours, greater than about 90 hours, greater than about 85 hours, greater than about 80 hours, greater than about 75 hours, greater than about 70 hours, greater than about 65 hours, greater than about 60 hours, greater than about 55 hours, greater than about 50 hours or greater than about 45 hours, and ranges therein. In some embodiments, the half-life is measured in a mouse.

In some embodiments, an anti-Flt-1 antibody, or antigen-binding fragment thereof, has a maximum serum concentration of greater than about 400 ug/mL, greater than 375 ug/mL, greater than about 350 ug/mL, greater than about 325 ug/mL, greater than about 300 ug/mL, greater than about 275 ug/mL, greater than about 250 ug/mL, greater than about 225 ug/mL, greater than about 200 ug/mL, greater than about 175 ug/mL, greater than about 150 ug/mL, greater than about 125 ug/mL, greater than about 100 ug/mL, greater than about 75 ug/mL or greater than about 50 ug/mL, and ranges therein. In some embodiments, the maximum serum concentration is measured in a mouse.

In some embodiments, an anti-Flt-1 antibody, or antigen-binding fragment thereof selectively binds Flt-1 and has minimal or no appreciable binding to other VEGF receptors. In some embodiments, an anti-Flt-1 antibody, or antigen-binding fragment thereof selectively binds Flt-1 and has minimal or no appreciable binding to VEGFR2 (Flk-1) and/or VEGFR3 (Flt-4).

In some embodiments, an anti-Flt-1 antibody, or antigen-binding fragment thereof has a ka of greater than about $1\times10^{-3}$ $M^{-1}$ $sec^{-1}$, greater than about $1\times10^{-4}$ $M^{-1}$ $sec^{-1}$, greater than about $1\times10^{-5}$ $M^{-1}$ $sec^{-1}$, greater than about $1\times10^{-6}$ $M^{-1}$ $sec^{-1}$, or greater than about $1\times10^{-7}$ $M^{-1}$ $sec^{-1}$ when binding to human Flt-1.

In some embodiments, an anti-Flt-1 antibody, or antigen-binding fragment thereof has a kd of greater than about $1\times10^{-3}$ $sec^{-1}$, greater than about $1\times10^{-4}$ $sec^{-1}$, greater than about $1\times10^{-5}$ $sec^{-1}$ or greater than about $1\times10^{-6}$ $sec^{-1}$ when binding to human Flt-1.

In some embodiments, an anti-Flt-1 antibody, or antigen-binding fragment thereof has a $K_D$ of greater than about $1\times10^{-8}$M, greater than about $1\times10^{-9}$M, greater than about $1\times10^{-10}$ M, greater than about $1\times10^{-11}$ M or greater than about $1\times10^{-12}$ M when binding to human Flt-1

In some embodiments an anti-Flt-1 antibody, or antigen-binding fragment thereof binds to soluble Flt-1. In particular embodiments, the binding is dose-dependent wherein higher concentrations of antibody, or antigen-binding fragment thereof, bind greater amounts of soluble Flt-1.

In some embodiments, an anti-Flt-1 antibody, or antigen-binding fragment thereof has a percent human identify of greater than about 99%, greater than about 98%, greater than about 97%, greater than about 96%, greater than about 95%, greater than about 94%, greater than about 93%, greater than about 92%, greater than about 91%, greater than about 90% or greater than about 80%.

In some embodiments, an anti-Flt-1 antibody, or antigen-binding fragment thereof has a percent human homology of greater than about 99%, greater than about 98%, greater than about 97%, greater than about 96%, greater than about 95%, greater than about 94%, greater than about 93%, greater than about 92%, greater than about 91%, greater than about 90% or greater than about 80%.

In some embodiments, an anti-Flt-1 antibody, or antigen-binding fragment thereof binds to Flt-1 protein. In some embodiment the Flt-1 protein is a recombinant protein, for example recombinant sFlt-1. In a particular embodiment, the anti-Flt-1 antibody, or antigen-binding fragment thereof binds human Flt-1 isoform 1 (NP_002010.2 GI:156104876; SEQ ID NO:90) (Table 2). In another embodiment the anti-Flt-1 antibody, or antigen-binding fragment thereof binds to human Flt-1 isoform X1 (XP_011533316.1 GI:767977511; SEQ ID NO:91). In another embodiment the anti-Flt-1 antibody, or antigen-binding fragment thereof binds to human Flt-1 isoform 2 precursor (NP_001153392.1 GI:229892220; SEQ ID NO:92). In yet another embodiment the anti-Flt-1 antibody, or antigen-binding fragment thereof binds to human Flt-1 isoform 3 precursor (NP_001153502.1 GI:229892300; SEQ ID NO:93). In another embodiment the anti-Flt-1 antibody, or antigen-binding fragment thereof binds to human Flt-1 isoform 4 precursor (NP_001153503.1 GI:229892302; SEQ ID NO:94).

In some embodiments the anti-Flt-1 antibody, or antigen-binding fragment thereof binds to a particular a epitope of the Flt-1 protein. For example, the anti-Flt-1 antibody or antigen-binding portion thereof binds to amino acids sequences as provided in Table 2.

least about 10 ug/mL or at least about 5 ug/mL, and ranges therein. In some embodiments, the peak serum antibody level is dose dependent.

In some embodiments, administration of an anti-Flt-1 antibody, or antigen-binding fragment thereof in vivo results in trough serum antibody levels of at least about 450 ug/mL, at least about 400 ug/mL, at least about 350 ug/mL, at least about 300 ug/mL, at least about 250 ug/mL, at least about 200 ug/mL, at least about 150 ug/mL, at least about 100 ug/mL, at least about 50 ug/mL or at least about 25 ug/mL, and ranges therein. In some embodiments, the trough serum antibody level is dose dependent.

In some embodiments, administration of an anti-Flt-1 antibody, or antigen-binding fragment thereof in vivo results in a decreased serum level of soluble Flt-1 as compared to a baseline level or as compared to a level in subjects administered vehicle alone. Typically, the baseline level is measured immediately before administration. In some embodiments, administration of the anti-Flt-1 antibody or antigen-binding fragment thereof results in a decreased serum level of soluble Flt-1 by at least about 95%, about 90%, about 80%, about 70%, about 60%, about 50%, about 40%, about 30%, about 20% or about 10% as compared to the baseline serum level of soluble Flt-1 immediately before administration. In some embodiments, administration of the anti-Flt-1 antibody, or antigen-binding fragment thereof results in a decreased serum level of soluble Flt-1 to less than about 4000 pg/mL, about 3500 pg/mL, about 3000 pg/mL, about 2500 pg/mL, about 2000 pg/mL, about 1750 pg/mL, about 1500 pg/mL, about 1250 pg/mL, about 1000 pg/mL, about 900 pg/mL, about 800 pg/mL, about 700 pg/mL, about 600 pg/mL, about 500 pg/mL, about 450 pg/mL, about 400 pg/mL, about 350 pg/mL, about 300 pg/mL, about 250 pg/mL, about 200 pg/mL, about 150 pg/mL, about, 100 pg/mL, about 50 pg/mL or about 10

TABLE 2

| amino acid position based on SEQ ID NO: 90 | Amino acid sequence | SEQ ID NO |
|---|---|---|
| 141-153 | EIPEIIHMTEGRE | SEQ ID NO: 95 |
| 193-206 | IISNATYKEIGLLT | SEQ ID NO: 96 |
| 130-138 | DTGRPFVEM | SEQ ID NO: 97 |
| 141-148 | EIPEIIHM | SEQ ID NO: 98 |
| 139-148 | YSEIPEIIHM | SEQ ID NO: 99 |
| 139-153 | YSEIPEIIHMTEGRE | SEQ ID NO: 100 |
| 178-206 | IPDGKRIIWDSRKGFIISNATYKEIGLLT | SEQ ID NO: 101 |
| 199-204 | YKEIGL | SEQ ID NO: 102 |
| 128-138 | ISDTGRPFVEM | SEQ ID NO: 103 |

In some embodiments, administration of an anti-Flt-1 antibody, or antigen-binding fragment thereof in vivo results in peak serum antibody levels of at least about 700 ug/mL, at least about 650 ug/mL, at least about 600 ug/mL, at least about 550 ug/mL, at least about 500 ug/mL, at least about 450 ug/mL, at least about 400 ug/mL, at least about 350 ug/mL, at least about 300 ug/mL, at least about 250 ug/mL, at least about 200 ug/mL, at least about 150 ug/mL, at least about 100 ug/mL, at least about 50 ug/mL, at least about 40 ug/mL, at least about 30 ug/mL, at least about 20 ug/mL, at pg/mL, and ranges therein. In some embodiments, administration of the anti-Flt-1 antibody, or antigen-binding fragment thereof results in a decreased serum level of soluble Flt-1 as compared to the serum level of soluble Flt-1 in a subject who is not administered the antibody or antigen-binding fragment thereof. In some embodiments, the decreased serum level of soluble Flt-1 is dose dependent.

In some embodiments, administration of an anti-Flt-1 antibody, or antigen-binding fragment thereof in vivo results in an increased serum level of VEGF as compared to a baseline level or as compared to a level in subjects treated with vehicle alone. Typically, the baseline level is measured immediately before treatment. In some embodiments, administration of the anti-Flt-1 antibody or antigen-binding fragment thereof results in an increased serum level of VEGF by at least about 95%, about 90%, about 80%, about 70%, about 60%, about 50%, about 40%, about 30%, about 20% or about 10% as compared to the baseline serum level of VEGF immediately before administration. In some embodiments, administration of the anti-Flt-1 antibody, or antigen-binding fragment thereof results in an increased serum level of VEGF to more than about 500 pg/mL, about 450 pg/mL, about 400 pg/mL, about 350 pg/mL, about 300 pg/mL, about 250 pg/mL, about 200 pg/mL, about 150 pg/mL, about 100 pg/mL about 50 pg/mL or about 25 pg/mL and ranges therein. In some embodiments, administration of the anti-Flt-1 antibody, or antigen-binding fragment thereof results in an increased serum level of VEGF as compared to the serum level of VEGF in a subject who is not treated. In some embodiments, the increased serum level of VEGF is dose dependent.

In some embodiments, administration of an anti-Flt-1 antibody, or antigen-binding fragment thereof in vivo results in increased angiogenesis in pulmonary tissue. In some embodiments, the increased angiogenesis is demonstrated by increased CD31 staining of an endothelial cell marker, for example, CD31. In some embodiments, the increased staining may be measured, for example, by measuring the percent CD31 positive area in pulmonary tissue of rats administered the anti-Flt-1 antibody, or antigen-binding fragment thereof. For example, the percent CD31 positive area in the pulmonary tissue of rats administered the anti-Flt-1 antibody, or antigen-binding fragment thereof may be at least about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4% or about 2.5% of the total tissue area. In a particular embodiment, the percent CD31 positive area in the pulmonary tissue of rats administered the anti-Flt-1 antibody may be significantly higher than the percent CD31 positive area in the pulmonary tissue of rats administered an isotype control antibody.

In some embodiments, the increased staining of an endothelial cell marker may be measured, for example, by measuring the normalized CD31 percent positivity in pulmonary tissue of rats administered the anti-Flt-1 antibody, or antigen-binding fragment thereof. In particular embodiments the increased CD31 staining the pulmonary tissue of rats administered the anti-Flt-1 antibody, or antigen-binding fragment thereof, is relative to CD31 staining measured in the pulmonary tissue of rats administered an isotype control antibody. For example, the normalized CD31 percent positivity in the pulmonary tissue of mice administered the anti-Flt-1 antibody, or antigen-binding fragment thereof may be at least about 200%, about 190%, about 180%, about 170%, about 160%, about 150%, about 140%, about 130%, about 120% or about 110%.

In some embodiments, an anti-Flt-1 antibody, or antigen-binding fragment thereof selectively binds human Flt-1, and has minimal or no appreciable binding to other mammalian Flt-1 receptors (e.g., with a binding affinity less than $10^{-7}$M or $10^{-6}$M). In some embodiments, an anti-Flt-1 antibody, or antigen-binding fragment thereof selectively binds human Flt-1 and does not bind to monkey Flt-1. In some embodiments, an anti-Flt-1 antibody, or antigen-binding fragment thereof selectively binds human Flt-1 and does not bind to mouse Flt-1.

In some embodiments, an anti-Flt-1 antibody, or antigen-binding fragment thereof binds human Flt-1 as well as monkey Flt-1. In some embodiments, anti-Flt-1 antibody, or antigen-binding fragment thereof binds to cynomolgus Flt-1. In some embodiments an anti-Flt-1 antibody, or antigen-binding fragment thereof binds human Flt-1 as well as mouse Flt-1.

In some embodiments, an anti-Flt-1 antibody, or antigen-binding fragment thereof, is selected from the group consisting of IgG, F(ab')$_2$, F(ab)$_2$, Fab', Fab, ScFvs, diabodies, triabodies and tetrabodies.

In some embodiments an anti-Flt-1 antibody, or antigen-binding fragment thereof, is IgG. In some embodiments an anti-Flt-1 antibody, or antigen-binding fragment thereof, is IgG1.

Engineered Constant Regions

In some embodiments, a suitable anti-Flt-1 antibody contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. Particularly suitable Fc domains include those derived from human or humanized antibodies.

It is contemplated that improved binding between Fc domain and the FcRn receptor results in prolonged serum half-life. Thus, in some embodiments, a suitable Fc domain (SEQ ID NO:104) comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Leu 234, Leu 235, Gly 237, Thr 250, Met 252, Ser 254, Thr 256, Thr 307, Glu 380, Met 428, His 433, and/or Asn 434 of human IgG1.

Some mutations in the Fc domain lead to reduced binding of the IgG with the FcRn receptor and thereby inhibit effector function. In some embodiments, a suitable Fc domain comprises one or more mutations at one or more positions corresponding to Leu 234, Leu 235 and Gly 237 of human IgG1. In a particular embodiment Leu 234 is mutated to Ala. In another embodiment Leu 235 is mutated to Ala. In yet another embodiment, Gly 237 is mutated to Ala.

In some embodiments, an anti-FLT-1 antibody or antigen-binding fragment contains a spacer and/or is linked to another entity. In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAP (SEQ ID NO:105) (GAG linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAGGGGG GAPGGGGGAAAAAGGGGGGAP (SEQ ID NO:106) (GAG2 linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAGGGGG GAPGGGGGAAAAAGGGGG GAP (SEQ ID NO:107) (GAG3 linker).

Production of Anti-Flt-1 Antibodies and Antigen Binding Fragments

A recombinant anti-Flt-1 antibody or antigen binding fragment suitable for the present invention may be produced by any available means. For example, a recombinant anti-Flt-1 antibody or antigen binding fragment may be recombinantly produced by utilizing a host cell system engineered to express a recombinant anti-Flt-1 antibody or antigen binding fragment-encoding nucleic acid.

Thus, the present invention further provides polynucleotide sequences encoding the various amino acid sequences described herein. In some embodiments, the present invention provides a polynucleotide sequence encoding an anti-Flt-1 antibody heavy chain or light chain amino acid sequences described herein, for example, any one of SEQ ID NOs:62-86 or SEQ ID NOs:108-110. In some embodiments, the present invention provides a polynucleotide sequence encoding a variable region of an anti-Flt-1 antibody heavy chain or light chain described herein, for example, any one of SEQ NOs:35-61. In some embodiments, the present invention provides a polynucleotide sequence encoding a CDR region of an anti-Flt-1 antibody heavy chain or light chain described herein, for example, any one of SEQ ID NOs:1-34. In some embodiments, the present invention provides a polynucleotide sequence encoding a constant region of an anti-Flt-1 antibody, for example, any one of SEQ ID NO:87-89. In some embodiments, the present invention provides a polynucleotide sequence encoding an Fc region of an anti-Flt-1 antibody described herein, for example, SEQ ID NO:104. In some embodiments, the present invention provides a polynucleotide sequence encoding a linker of an anti-Flt-1 antibody described herein, for example, SEQ ID NOs:105-107.

In some embodiments, a polynucleotide sequence encoding an anti-Flt-1 antibody heavy chain, light chain, variable region, CDR region, Fc region or linker region further includes a sequence encoding a signal peptide. As a non-limiting example, a suitable signal peptide includes amino acid sequence MGWSCIILFLVATATGVHS (SEQ ID NO:111).

Various polynucleotide sequences described herein may be embodied in various vector systems for expression of recombinant anti-Flt-1 antibodies or antigen-binding fragment thereof.

Where antibodies are recombinantly produced, any expression system can be used. To give but a few examples, known expression systems include, for example, egg, baculovirus, plant, yeast, or mammalian cells.

In some embodiments, recombinant anti-Flt-1 antibody or antigen binding fragments suitable for the present invention are produced in mammalian cells. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); and monkey kidney CV1 line transformed by SV40 (COS-7, ATCC CRL 1651).

In some embodiments, the present invention provides recombinant anti-Flt-1 antibody or antigen binding fragment produced from human cells. In some embodiments, the present invention provides anti-Flt-1 antibody or antigen binding fragment produced from CHO cells.

Pharmaceutical Compositions Containing the Antibodies of the Invention

The present invention further provides pharmaceutical compositions comprising therapeutically active ingredients in accordance with the invention (e.g. anti-Flt-1 antibody, or antigen-binding fragment thereof), together with one or more pharmaceutically acceptable carrier or excipient. Such pharmaceutical compositions may optionally comprise one or more additional therapeutically-active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient or carrier and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or carrier, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient or carrier, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium or carrier is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient or carrier is at least 95%, at least 96%, at least 97%, at least 98%, at least 99%, or 100% pure. In some embodiments, an excipient or carrier is approved for use in humans and for veterinary use. In some embodiments, an excipient or carrier is approved by United States Food and Drug Administration. In some embodiments, an excipient or carrier is pharmaceutical grade. In some embodiments, an excipient or carrier meets the standards of the United States Pharmacopoeia (USP), the European Pharmacopoeia (EP), the British Pharmacopoeia, and/or the International Pharmacopoeia.

Pharmaceutically acceptable excipients or carriers used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients or carriers may optionally be included in pharmaceutical formulations. Excipients or carriers such as cocoa butter and suppository waxes, coloring agents, coating agents, sweetening, flavoring, and/or perfuming agents can be present in the composition, according to the judgment of the formulator.

Suitable pharmaceutically acceptable excipients or carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

General considerations in the formulation and/or manufacture of pharmaceutical agents may be found, for example, in Remington: *The Science and Practice of Pharmacy* 21$^{st}$ ed., Lippincott Williams & Wilkins, 2005 (incorporated herein by reference).

Routes of Administration

An anti-Flt-1 antibody or antigen binding fragment described herein (or a composition or medicament containing an anti-Flt-1 antibody or antigen binding fragment described herein) is administered by any appropriate route. In some embodiments, an anti-Flt-1 antibody or antigen binding fragment protein or a pharmaceutical composition containing the same is administered parenterally. Parenteral administration may be intravenous, intradermal, intrathecal, inhalation, transdermal (topical), intraocular, intramuscular, subcutaneous, intramuscular, and/or transmucosal administration. In some embodiments, an anti-Flt-1 antibody or antigen binding fragment or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, an anti-Flt-1 antibody or antigen binding fragment thereof or a pharmaceutical composition containing the same is administered intravenously. In some embodiments, an anti-Flt-1 antibody or antigen binding fragment thereof or a pharmaceutical composition containing the same is administered intra-arterially. In some embodiments, an anti-Flt-1 antibody or antigen binding fragment or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of an anti-Flt-1 antibody or antigen binding fragment to one or more target tissues including but not limited lungs and heart.

Dosage Forms and Dosing Regimen

In some embodiments, a composition is administered in a therapeutically effective amount and/or according to a dosing regimen that is correlated with a particular desired outcome (e.g., with treating or reducing risk for a chronic lung disorder, such as bronchopulmonary dysplasia).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an anti-Flt-1 antibody or antigen binding fragment thereof is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a chronic lung disorder, such as bronchopulmonary dysplasia.

In some embodiments, a formulation comprising an anti-Flt-1 antibody or antigen binding fragment described herein administered as a single dose. In some embodiments, a formulation comprising an anti-Flt-1 antibody or antigen binding fragment described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an anti-Flt-1 antibody or antigen binding fragment described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an anti-Flt-1 antibody or antigen binding fragment described herein is administered at regular intervals indefinitely. In some embodiments, a formulation comprising an anti-Flt-1 antibody or antigen binding fragment described herein is administered at regular intervals for a defined period. In some embodiments, a formulation comprising an anti-Flt-1 antibody or antigen binding fragment described herein is administered prenatally. In some embodiments, a formulation comprising an anti-Flt-1 antibody or antigen binding fragment described herein is administered postnatally.

In some embodiments, a formulation comprising an anti-Flt-1 antibody or antigen binding fragment described herein is administered at a dose of about 0.5 mg/kg body weight, about 1.0 mg/kg body weight, about 10 mg/kg body weight or about 20 mg/kg body weight.

In some embodiments, a formulation comprising an anti-Flt-1 antibody or antigen binding fragment described herein is administered at a dose ranging from about 0.5 mg/kg body weight to about 20 mg/kg body weight, for example about 1 mg/kg body weight to about 10 mg/kg body weight.

In some embodiments, a formulation comprising an anti-Flt-1 antibody or antigen binding fragment described herein is administered to an adult at a unit dose of about 35 mg, about 70 mg, about 700 mg or about 1400 mg. In some embodiments, a formulation comprising an anti-Flt-1 antibody or antigen binding fragment described herein is administered at a dose ranging from about 35 mg to about 1400 mg, for example about 70 mg to about 700 mg.

In some embodiments, a formulation comprising an anti-Flt-1 antibody or antigen binding fragment described herein is administered to an infant at a unit dose of about 2 mg, about 4 mg, about 40 mg or about 80 mg. In some embodiments, a formulation comprising an anti-Flt-1 antibody or antigen binding fragment described herein is administered at a dose ranging from about 2 mg to about 80 mg, for example about 4 mg to about 40 mg. In some embodiments, administration of an anti-Flt-1 antibody, or an antigen binding fragment thereof reduces the intensity, severity, or frequency, or delays the onset of at least one BPD sign or symptom. In some embodiments administration of an anti-Flt-1 antibody, or an antigen binding fragment thereof reduces the intensity, severity, or frequency, or delays the onset of at least one BPD sign or symptom selected from the group consisting of lung inflammation, lung scarring, impaired lung growth, early lung injury, prolonged respiratory insufficiency, lung infections, exercise intolerance, and adverse neurological outcome.

Combination Therapy

In some embodiments, an anti-Flt-1 antibody or antigen binding fragment is administered in combination with one or more known therapeutic agents (e.g., corticosteroids) currently used for treatment of a muscular dystrophy. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. In Vitro Efficacy of Anti-Flt-1 Antibodies

Fetal Pulmonary Artery Endothelial Cell Isolation

Pulmonary artery endothelial cells (PAECs) are harvested from the proximal pulmonary arteries of late gestation control fetal sheep at day 135 (day 147 term). Immunohistochemistry with standard endothelial markers confirms the cell phenotype. Low-passage PAECs (p4-5) are then exposed to ETX, VEGF, sFlt1 or anti-FM alone or in combination.

Growth of PAECs While Exposed to ETX, VEGF, sFlt1 and Anti-Flt1

Fetal PAECs are plated in triplicate at 50,000 cells/well in DMEM with 10% FBS into 12 well plates and allowed to adhere overnight in 21% oxygen. The following day (day 0) the cells are washed twice with PBS. DMEM with 2.5% FBS with VEGF, ETX, sFlt1, or anti-Flt1 (alone or in combination) is then added, and cells incubated in 21% oxygen. Final concentrations of exogenous factors are as follows: VEGF 50 ng/mL, ETX 1 ng/mL, sFlt1 114 ng/mL and anti-Flt1 1800 ng/mL. Experimental media is changed daily and cells were counted on day 3 after removing cells with 0.25% trypsin and counted with a cell counter (Beckman Coulter; Fullerton, Calif.). Growth studies with treatment are performed in DMEM with 2.5% FBS, based on previous studies that determined that this was the lowest serum concentration that supported fetal PAEC survival with some proliferation.

PAEC Tube Formation Assay

To assay in vitro angiogenesis, we cross-linked rat-tail collagen using 0.2% Flavin mononucleotide and a UV Stratalinker 1800 (Stratagene). 50,000 cells/well are added in serum free DMEM media supplemented with ETX, VEGF, sFlt1 and anti-Flt1 (alone or in combination) and each condition is tested in triplicate for each animal. PAECs are then incubated for 12-18 hours under 3% oxygen conditions based on previous studies that determined tube formation is more robust in 3% compared to 21% oxygen. Branch-point counting is performed in blinded fashion under ×10 magnification from each of three wells with three to four field of view per well. Wells are imaged using an Olympus IX71 fluorescence microscope (Olympus).

Statistical Analysis

Statistical analysis is performed with the Prism software package (v. 5.0a, GraphPad). Repeated measures one-way analysis of variance (ANOVA) with Bonferroni post-test analysis are performed. P values less than 0.05 are considered significant.

Administration of Anti-Flt-1 Antibody to PAECs Exposed to sFLT

Cells are treated with recombinant human VEGF (50 ng/mL), recombinant human soluble Flt-1 (sFLT, 114 ng/mL) or antibody for human soluble Flt-1 (a-sFLT, 1800 ng/mL) either alone or in combination. PAEC growth is measured 3 days after treatment and the number of tube branch points is measured 24 hours after treatment.

Results

Treatment with sFLT and VEGF decreases the number of PAECs compared to cells treated only with VEGF and treatment, indicating that sFLT prevents VEGF from promoting cell growth. When both sFLT and a-sFLT are combined with VEGF, the number of PAECs is brought up to the levels seen when cells were treated with only VEGF, demonstrating that a-sFLT inhibits the sFLT-induced decrease in cell growth.

Treatment with VEGF alone increases the number of tube branch points, as does treatment with VEGF and a-sFLT. Contrastingly, treatment with VEGF and sFLT decreases the number of branch points as compared with the cells treated with only VEGF. When both sFLT and a-sFLT are combined with VEGF, the number of branch points is comparable to the number seen in the VEGF only group, demonstrating that a-sFLT inhibits the sFLT-induced decrease in the number of branch points.

Administration of Anti-Flt-1 Antibody to PAECs Exposed to ETX

Cells are treated with either VEGF (50 ng/mL), endotoxin (ETX, 1 ng/mL), VEGF+ETX, EXT+a-sLFT (1800 ng/mL) or EXT+VEGF+a-sFLT. PAEC growth is measured 3 days after treatment and the number of tube branch points is measured 24 hours after treatment.

Results

PAEC growth is increased after treatment with VEGF compared to control (CTL) and PAECs treated with only ETX showed decreased growth compared to control. The combination of either VEGF or a-sFLT with ETX brings cells numbers up to the level seen in the control group, as does treatment with ETX, VEGF and a-sFLT, which indicates that treatment with either VEGF or a-sFLT can reverse the detrimental effects of ETX on PAEC growth.

The number of branch points increases after treatment with VEGF only and cells treated with only ETX shows a decreased number of branch points compared to both the control and VEGF treated groups. The combination of either VEGF or a-sFLT with ETX brings the number of branch points up to the level seen in the control group, as does treatment with ETX, VEGF and a-sFLT, which indicates that treatment with either VEGF or a-sFLT can reverse the detrimental effects of ETX on the number of branch points in tubes.

Example 2. In Vivo Efficacy of Anti-Flt-1 Antibodies in ETX Model of BPD

Animals

All procedures and protocols are approved by the Animal Care and Use Committee at the University of Colorado Health Sciences Center. Timed pregnant Sprague-Dawley rats are purchased from Charles River Laboratories (Wilmington, Mass.) and maintained in room air at Denver's altitude (1,600 m; barometric pressure, 630 mmHg; inspired oxygen tension, 122 mmHg) for at least 1 week before giving birth. Animals are fed ad libitum and exposed to day-night cycles alternatively every 12 hours. Rats are killed with an intraperitoneal injection of pentobarbital sodium (0.3 mg/g body weight; Fort Dodge Animal Health, Fort Dodge, Iowa).

Animal Model and Study Design

Intra-Amniotic ETX, Vitamin D and Anti-sFLT Administration

An animal model of chorioamnionitis is utilized. At 20 days gestation (term: 22 days), pregnant rats are prepared for receiving intra-amniotic (IA) injections. The timing of injection during the late canalicular stage of lung development in the rat is selected to parallel the similar stage of human lung development in 24 to 26 week premature newborns who are at the highest risk for BPD. After premedication with buprenorphine (0.01-0.05 mg/kg, subcutaneous injection), laparotomy is performed under general anesthesia with 1-2% isoflurane inhalation via facemask (anesthesia machine: Matrx by Midmark, model VIP3000). During anesthesia and laparotomy, pregnant rats are kept on a heating pad for preventing hypothermia. Pregnant rats are randomly assigned to saline control (CTR), endotoxin (ETX), or ETX+vitamin D (vit D) group in one study or to saline control (CTR), endotoxin (ETX) or ETX+anti-sFLT in the other study. The CTR groups receives 50 µl of normal 136 saline per amniotic sac, the ETX groups receives 10 µg of *Escherichia coli* 055:B55 ETX (Sigma Chemical, St. Louis, Mo.) diluted to 50 µl with normal saline per sac, the ETX+vit D group receives 10 µg of *Escherichia coli* 055:B55 ETX and 50 pg diluted to 50 µl with normal saline and the ETX+anti-sFLT group receives 10 µg of *Escherichia coli* 055:B55 ETX and low dose (1× molar equivalent) or high dose (10× molar equivalent) anti-sFlt1 antibody. Under sterile preparation, a midline abdominal incision of 3-4 cm in length is made to expose the amniotic sacs for IA injections. The amniotic sac closest to the right ovary is first identified and injected, and then in a counterclockwise sequence each sac is identified and injected with a maximum of 10 sacs injected per dam. Injections are limited to 10 sacs to prevent maternal mortality due to systemic toxicities from accumulating doses of IA ETX. The dose of ETX was established from previous studies that demonstrated ETX at lower doses (1-5 µg/sac) failed to induce abnormal lung structure at 14 days of age. The dose of vit D was established again from previous studies demonstrating vit D at higher doses (500 ng/gm) produced subcutaneous calcium deposits noted in rat pups. The abdominal incision is closed with nylon sutures. Bupivacaine (1-2 mg/kg, intramuscular injection) is applied over the incision wound for postoperative pain control. Pregnant rats were monitored closely to ensure arousal within 10 minutes after surgery, and rats were placed back to the cages and were monitored for activity and for signs of bleeding or infection.

Cesarean Section

Two days after IA injections, cesarean section is performed on pregnant rats under general anesthesia with isoflurane inhalation, as described above. The fetus in the amniotic sac closest to the right ovary is first delivered, which is followed by delivery of the rest of the fetuses in a counterclockwise sequence, to identify fetuses exposed to IA injections. Cesarean sections are performed instead of allowing vaginal deliveries in order to identify fetuses exposed to specific IA injections, based on the order of the amniotic sacs and their anatomic locations related to the ovaries. All of the rat pups in the injected amniotic sacs are delivered within 5 minutes after onset of anesthesia. Mother rats are then euthanized with pentobarbital sodium. Newborn rats are immediately dried and placed on a heating pad to avoid hypothermia. Pups receive no supplemental oxygen or artificial ventilation at birth. Within 30 minutes after birth, pups are weighed and either sacrificed for histology or placed with foster mother rats to be raised through 14 days. Rat lungs are harvested at birth and 14 days of age for histological assessment. Survival of the infant rats is monitored and recorded daily from birth throughout the study period. Survival rate is calculated as the number of survived pups divided by the number of sacs that received intra-amniotic injection in each given litter.

Study Measurements

Tissue for Histological Analysis

Animals are killed with intra-peritoneal pentobarbital sodium. A catheter is placed in the trachea and the lungs are inflated with 4% paraformaldehyde and maintained at 20 cm $H_2O$ pressure for 60 minutes. A ligature is tightened around the trachea to maintain pressure and the tracheal cannula is removed. Lungs are immersed in 4% paraformaldehyde at room temperature overnight for fixation. A 2-mm thick transverse section is taken from the mid-plane of right lower lobe and left lobe of the fixed lungs per animal, respectively. Two sections from each animal are processed and embedded in paraffin wax for study.

Bronchoalveolar Lavage (BAL)

Bronchoalveolar lavage was performed on the day of birth (Day 0) according to standard techniques and sFLT levels in the lung were measured.

Radial Alveolar Counts (RAC)

Alveolarization is assessed by the RAC method of Emery and Mithal as described (Cooney T P, Thurlbeck W M. The radial alveolar count method of Emery and Mithal: a reappraisal 1-postnatal lung growth. Thorax 37:572-579, 1982; Cooney T P, Thurlbeck W M. The radial alveolar count method of Emery and Mithal: a reappraisal 2-intrauterine and early postnatal lung growth. Thorax 37:580-583, 1982). Respiratory bronchioles are identified as bronchioles lined by epithelium in one part of the wall. From the center of the respiratory bronchiole, a perpendicular line is dropped to the edge of the acinus connective tissues or septum or pleura, and the number of septae intersected by this line was counted.

Statistical Analysis

Statistical analysis is performed with the Prism software package (v. 5.0a, GraphPad). Repeated measures one-way analysis of variance (ANOVA) with Bonferroni post-test analysis are performed. P values less than 0.05 are considered significant.

Results sFLT levels are increased in rats exposed to ETX in utero compared to the control group and treatment with Vitamin D decreased the levels of sFLT to the level seen in the control group. This demonstrates that treatment with Vitamin D could be used as a therapeutic for treating BPD via the action of Vitamin D on levels of sFLT in the lungs.

As shown by morphometric analysis, RAC is decreased in rats exposed to ETX in utero compared to the control group and in utero dosing with anti-sFLT in rats exposed to ETX increased RAC compared to the group only exposed to ETX. This demonstrates that treatment with anti-sFLT could be used as a therapeutic for treating BPD.

Example 4. In Vivo Efficacy of Anti-Flt-1 Antibodies in sFLT Model of BPD

Animals

All procedures and protocols are approved by the Animal Care and Use Committee at the University of Colorado Health Sciences Center. Pregnant Sprague-Dawley rats are purchased from Charles River Laboratories (Wilmington, Mass.) and maintained in room air at Denver's altitude (1,600 meters; barometric pressure, 630 mmHg; inspired oxygen tension, 122 mmHg) for at least 1 week before giving birth. Animals are fed ad libitum and exposed to day-night cycles alternatively every 12 hours. Rats are killed with an intraperitoneal injection of pentobarbital sodium (0.3 mg/g body wt; Fort Dodge Animal Health, Fort Dodge, Iowa).

Study Design

Intra-Amniotic sFlt-1 Administration

At 20 days gestation (term: 22 days), pregnant rats are prepared for receiving intra-amniotic injections. The timing of injection during the late canalicular stage of lung development in the rat was selected to parallel a similar stage of human lung development in 24- to 26-week premature newborns who are at the highest risk for BPD. After premedication with buprenorphine (0.01-0.05 mg/kg, intramuscular injection), laparotomy is performed on pregnant rats under general anesthesia with 1-2% isoflurane inhalation via a face mask (Anesthesia machine: Matrx by Midmark, model VIP3000). During anesthesia and laparotomy, pregnant rats are kept on a heating pad for preventing hypothermia. Pregnant rats are randomly assigned to saline control or sFlt-1 group; the saline group received 50 µL of normal saline per amniotic sac, and the sFlt-1 group receives 50 µg of recombinant human sFlt-1-Fc (R&D Systems, Minneapolis, Minn.) diluted to 50 µL with normal saline per sac. One sFLT group received a low dose (1× molar equivalent) of anti-sFLT and the other received a high dose (10× molar equivalent) of anti-sFLT. Under sterile preparation, a midline abdominal incision of 3-4 cm in length is made to expose the amniotic sacs for intra-amniotic injections. The amniotic sac closest to the right ovary is first identified and injected, and then in a counterclockwise sequence each sac is identified and injected with a maximum of 10 sacs injected per dam. Limiting sFlt-1 injections to 10 sacs per pregnant rat is to achieve a consistent total dose of sFlt-1 on the individual mother rats, given intra-amniotic sFlt-1 is absorbed into the maternal circulation through an intramembranous pathway, which is characterized by a microscopic network of fetal vasculature on the fetal surface of the placenta to mediate the transfer of intraamniotic substances into fetal and maternal circulations. Similarly, considering the communication between the amniotic cavity and maternal and fetal circulations through the intramembranous pathway, intra-amniotic saline is given in separate litters to serve as controls. The total number of amniotic sacs in each mother rat is examined and recorded during laparotomy. The abdominal incision is closed with nylon sutures. Bupivacaine (1-2 mg/kg, subcutaneous injection) is applied over the incision wound for postoperative pain control. Pregnant rats are monitored closely to ensure arousal within 10 minutes after surgery, and rats are placed back to the cages and were monitored for activity, ability to drink and eat, and for signs of bleeding or infection.

Cesarean Section

Two days after intra-amniotic injections, cesarean section is performed on pregnant rats under general anesthesia with isoflurane inhalation, as described above. The fetus in the amniotic sac closest to the right ovary is first delivered, which was followed by delivery of the rest of the fetuses in a counterclockwise sequence, to identify fetuses exposed to intra-amniotic injections. The total number of amniotic sacs in each mother rat is further verified at the time of delivery. The main reason for performing cesarean section instead of allowing vaginal delivery is to identify the fetuses exposed to intra-amniotic injections, based on the order of the amniotic sacs and their anatomic locations related to the ovaries. All of the rat pups in the injected amniotic sacs are delivered within 5 minutes after the onset of anesthesia. Maternal rats are then killed with pentobarbital sodium. Newborn rats are immediately placed on a heating pad to avoid hypothermia and are dried manually with gauze sponges. Pups receive no supplemental oxygen or artificial ventilation at birth. The survival rate at birth is recorded. Within 30 minutes after birth, the pups are weighed and placed with foster mother rats in regular cages. For the first 24 h of life, the newborn pups are monitored closely for mortality or signs of respiratory distress.

Rat lungs are harvested at birth for Western blot analysis and at birth and 14 days of age for histological assessment. Hearts are dissected and weighed at birth and 7 and 14 days of age. Three to nine rats are studied in each group for each measurement at each time point. Survival of the infant rats is monitored and recorded daily from birth throughout the study period. Survival rate is calculated as the number of survived pups divided by the number of sacs that received intra-amniotic injection in each given litter. Body weight is measured at birth and at the time of being killed for study measurements.

Study Measurements

Tissue for Histological Analysis

Animals are killed with intraperitoneal pentobarbital sodium. A catheter is placed in the trachea, and the lungs are inflated with 4% paraformaldehyde and maintained at 20 cm $H_2O$ pressure for 60 min. A ligature is tightened around the trachea to maintain pressure, and then the tracheal cannula is removed. Lungs are then immersed in 4% paraformaldehyde at room temperature for 24 hours for fixation. A 2-mm-thick transverse section is taken from the midplane of the right lower lobe and left lobe of the fixed lungs per animal, respectively, to process and embed in paraffin wax.

Immunohistochemistry

Slides with 5 µm paraffin sections are stained with hematoxylin and eosin for assessing alveolar structures and with von Willebrand Factor (vWF), an endothelial cell-specific marker, for quantifying vessel density.

Pulmonary Vessel Density

Pulmonary vessel density is determined by counting vWF-stained vessels with an external diameter at 50 µm or less per high-power field. The fields containing large airways or vessels with external diameter>50 µm are avoided.

Radial Alveolar Counts (RAC)

Alveolarization is assessed by the RAC method of Emery and Mithal as described (Cooney T P, Thurlbeck W M. The radial alveolar count method of Emery and Mithal: a reappraisal 1-postnatal lung growth. Thorax 37:572-579, 1982; Cooney T P, Thurlbeck W M. The radial alveolar count method of Emery and Mithal: a reappraisal 2-intrauterine and early postnatal lung growth. Thorax 37:580-583, 1982). Respiratory bronchioles are identified as bronchioles lined by epithelium in one part of the wall. From the center of the respiratory bronchiole, a perpendicular line is dropped to the edge of the acinus connective tissues or septum or pleura, and the number of septae intersected by this line is counted.

Indices of Right Ventricular Hypertrophy

The right ventricle (RV) and left ventricle plus septum (LV+S) are dissected and weighed. The ratios of RV to LV+S weights (RV/LV+S %) and RV/body weights (RV/BW %) are determined to evaluate right ventricular hypertrophy (RVH).

Statistical Analysis

Statistical analysis is performed with the InStat 3.0 software package (GraphPad Software, San Diego, Calif.). Statistical comparisons are made between groups using t-test or ANOVA with Newman-Keuls post hoc analysis for significance. $P<0.05$ is considered significant.

Results

Pulmonary vessel density is increased in animals treated with sFLT+anti-sFLT compared to those treated only with sFLT.

Alveolarization is assessed by the radial alveolar count (RAC) method. When analyzed by morphometric analysis, sFLT rats have significantly decreased RAC ($P<0.001$) compared with the control group (CTL). Treatment with the low dose of a-sFLT significantly increases RAC ($P<0.01$) compared to the sFLT group. This indicates that treatment with a-sFLT can reverse the decrease in alveolarization caused by sFLT.

Right ventricular hypertrophy is assessed by weighing the right ventricle (RV) and left ventricle plus septum (LV+S) and calculating the ratio. Animals exposed to sFLT have an increased RV/(LV+S) ratio compared to the control group. Treatment with the low dose of a-sFLT decreases the RV/(LV+S) ratio compared to the sFLT group. This indicates that treatment with a-sFLT can reverse the right ventricular hypertrophy caused by sFLT.

The ratio of the right ventricle (RV) to body weight is determined to evaluation right ventricular hypertrophy. Animals exposed to sFLT have an increased RV/body weight ratio compared to the control group. Treatment with the low dose of a-sFLT significantly decreases the RV/body weight ratio compared to the sFLT group. This indicates that treatment with a-sFLT can reverse the right ventricular hypertrophy caused by sFLT.

Example 5. In vivo Efficacy of anti-Flt-1 Antibody in an Endotoxin (ETX) Induced Model of BPD Study Design Intra-Amniotic sFlt-1 and ETX Administration At 20 days gestation (term: 22 days), pregnant rats are prepared for receiving intra-amniotic injections. Pregnant rats are randomly assigned to saline control or ETX (endotoxin) group; the saline group receives normal saline injection into the amniotic sac, and the ETX group receives 10 µg endotoxin per sac. Following intra-amniotic administration, the abdominal incision is closed and rats are monitored closely to ensure arousal after surgery.

Cesarean Section and Treatment

Two days after intra-amniotic injections, cesarean section is performed on pregnant rats under general anesthesia, as described above. Pups are treated twice a week for two weeks with 1 mg/kg anti-sFLT monoclonal antibody, 10 mg/kg anti-sFLT monoclonal antibody or 10 mg/kg IgG control (mouse IgG1 isotype control).

Study Measurements

At day 14, rat lungs are harvested for morphometric analysis and for histological assessment. Body weight of the animals is measured at birth and at the time of sacrifice. Lungs are fixed after inflation with 4% paraformaldehyde at 20 cm $H_2O$. Distal airspace structure is assessed by Radial Alveolar Counts (RAC). Hearts are collected to determine right ventricular hypertrophy (RV/LS+S weights)

Body Weight

The body weight of animals is measured to determine if postnatal anti-Flt-1 monoclonal antibody treatment improves body weight following antenatal ETX treatment. Animals administered ETX in utero followed by postnatal treatment with IgG (control) or anti-Flt-1 mAb (1 mg/kg or 10 mg/kg) are weighed. Animals receiving only ETX or ETX+IgG weigh significantly less than control animals. The weight of animals receiving ETX+either dose of anti-Flt-1 mAb is not significantly different from the weight of control animals. These data indicate that animals given postnatal anti-Flt-1 mAb can have a growth advantage in an endotoxin induced model of BPD.

Radial Alveolar Counts (RAC)

Radial alveolar count is measured to determine if postnatal anti-Flt-1 monocolonal antibody treatment improves alveolar growth after antenatal ETX treatment. The lungs of animals administered ETX in utero followed by postnatal treatment with IgG (control treatment) or anti-Flt-1 monoclonal antibody (1 mg/kg or 10 mg/kg) are studied. Animals receiving only ETX or ETX+IgG demonstrate significantly reduced alveolar growth as compared to control animals. Alveolar growth in animals receiving ETX+10 mg/kg of anti-Flt-1 monoclonal antibody is significantly better than alveolar growth in animals receiving ETX alone. These data indicate that animals given postnatal anti-Flt-1 monoclonal antibody can have improved lung structure in an endotoxin induced model of BPD.

Indices of Right Ventricular Hypertrophy

The right ventricle is measured to determine if postnatal anti-Flt-1 monoclonal antibody treatment prevents right ventricular hypertrophy (RVH) after antenatal ETX treatment. The hearts of animals administered ETX in utero followed by postnatal treatment with IgG (control treatment) or anti-Flt-1 monoclonal antibody (1 mg/kg or 10 mg/kg) are studied. Animals receiving only ETX or ETX+IgG demonstrate a significantly increased right ventricle ratio as compared to control animals. Right ventricle ratio in animals receiving ETX+either dose of anti-Flt-1 monocolonal antibody is not significantly different from the right ventricle ratio of control animals. Right ventricle ratio in animals receiving ETX+either dose of anti-Flt-1 monocolonal antibody is significantly different from the right ventricle ratio of animals receiving ETX. These data indicate that animals given postnatal anti-Flt-1 monoclonal antibody can have diminished pulmonary hypertension in an endotoxin induced model of BPD.

Lung Structure

Lung structure and pulmonary vessel density is assessed to determine if postnatal anti-Flt-1 monoclonal antibody treatment restores lung structure after antenatal ETX treatment. Lungs of animals administered ETX in utero followed by postnatal treatment with IgG (control treatment) or anti-Flt-1 monoclonal antibody (1 mg/kg or 10 mg/kg) are studied. These data indicate that postnatal anti-sFlt-1 monoclonal antibody can restore lung structure in experimental chorioamnionitis.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

TABLE 3

```
Human Flt-1 amino acid sequence isoform 1 (NP_002010.2 GI:156104876;
SEQ ID NO: 90)
    1    MVSYWDTGVL LCALLSCLLL TGSSSGSKLK DPELSLKGTQ HIMQAGQTLH LQCRGEAAHK

61    WSLPEMVSKE SERLSITKSA CGRNGKQFCS TLTLNTAQAN HTGFYSCKYL AVPTSKKKET

121    ESAIYIFISD TGRPFVEMYS EIPEIIHMTE GRELVIPCRV TSPNITVTLK KFPLDTLIPD

181    GKRIIWDSRK GFIISNATYK EIGLLTCEAT VNGHLYKTNY LTHRQTNTII DVQISTPRPV

241    KLLRGHTLVL NCTATTPLNT RVQMTWSYPD EKNKRASVRR RIDQSNSHAN IFYSVLTIDK

301    MQNKDKGLYT CRVRSGPSFK SVNTSVHIYD KAFITVKHRK QQVLETVAGK RSYRLSMKVK

361    AFPSPEVVWL KDGLPATEKS ARYLTRGYSL IIKDVTEEDA GNYTILLSIK QSNVFKNLTA

421    TLIVNVKPQI YEKAVSSFPD RALYPLGSRQ ILTCTAYGIP QPTIKWFWHP CNHNHSEARC

481    DFCSNNEESF ILDADSNMGN RIESITQRMA IIEGKNKMAS TLVVADSRIS GIYICIASNK

541    VGTVGRNISF YITDVPNGFH VNLEKMPTEG EDLKLSCTVN KFLYRDVTWI LLRTVNNRTM

601    HYSISKQKMA ITKEHSITLN LTIMNVSLQD SGTYACRARN VYTGEEILQK KEITIRDQEA

661    PYLLRNLSDH TVAISSSTTL DCHANGVPEP QITWFKNNHK IQQEPGIILG PGSSTLFIER

721    VTEEDEGVYH CKATNQKGSV ESSAYLTVQG TSDKSNLELI TLTCTCVAAT LFWLLLTLFI

781    RKMKRSSSEI KTDYLSIIMD PDEVPLDEQC ERLPYDASKW EFARERLKLG KSLGRGAFGK
```

TABLE 3-continued

```
 841    VVQASAFGIK KSPTCRTVAV KMLKEGATAS EYKALMTELK ILTHIGHHLN VVNLLGACTK

901    QGGPLMVIVE YCKYGNLSNY LKSKRDLFFL NKDAALHMEP KKEKMEPGLE QGKKPRLDSV

961    TSSSESFASSG FQEDKSLSDV EEEEDSDGFY KEPITMEDLI SYSFQVARGM EFLSSRKCIH

1021    RDLAARNILL SENNVVKICD FGLARDIYKN PDYVRKGDTR LPLKWMAPES IFDKIYSTKS

1081    DVWSYGVLLW EIFSLGGSPY PGVQMDEDFC SRLREGMRMR APEYSTPEIY QIMLDCWHRD

1141    PKERPRFAEL VEKLGDLLQA NVQQDGKDYI PINAILTGNS GFTYSTPAFS EDFFKESISA

1201    PKFNSGSSDD VRYVNAFKFM SLERIKTFEE LLPNATSMFD DYQGDSSTLL ASPMLKRFTW

1261    TDSKPKASLK IDLRVTSKSK ESGLSDVSRP SFCHSSCGHV SEGKRRFTYD HAELERKIAC

1321    CSPPPDYNSV VLYSTPPI
```

Human Flt-1 amino acid sequence, isoform X1 (XP_011533316.1 GI:767977511; SEQ ID NO: 91)
```
   1    MVSYWDTGVL LCALLSCLLL TGSSSGSKLK DPELSLKGTQ HIMQAGQTLH LQCRGEAAHK

61    WSLPEMVSKE SERLSITKSA CGRNGKQFCS TLTLNTAQAN HTGFYSCKYL AVPTSKKKET

121    ESAIYIFISD TGRPFVEMYS EIPEIIHMTE GRELVIPCRV TSPNITVTLK KFPLDTLIPD

181    GKRIIWDSRK GFIISNATYK EIGLLTCEAT VNGHLYKTNY LTHRQTNTII DVQISTPRPV

241    KLLRGHTLVL NCTATTPLNT RVQMTWSYPD EKNKRASVRR RIDQSNSHAN IFYSVLTIDK

301    MQNKDKGLYT CRVRSGPSFK SVNTSVHIYD KAFITVKHRK QQVLETVAGK RSYRLSMKVK

361    AFPSPEVVWL KDGLPATEKS ARYLTRGYSL IIKDVTEEDA GNYTILLSIK QSNVFKNLTA

421    TLIVNVKPQI YEKAVSSFPD RALYPLGSRQ ILTCTAYGIP QPTIKWFWHP CNHNHSEARC

481    DFCSNNEESF ILDADSNMGN RIESITQRMA IIEGKNKMAS TLVVADSRIS GIYICIASNK

541    VGTVGRNISF YITDVPNGFH VNLEKMPTEG EDLKLSCTVN KFLYRDVTWI LLRTVNNRTM

601    HYSISKQKMA ITKEHSITLN LTIMNVSLQD SGTYACRARN VYTGEEILQK KEITIRDQEA

661    PYLLRNLSDH TVAISSSTTL DCHANGVPEP QITWFKNNHK IQQEPDADPH IQKADCTFFF
```

Human Flt-1 amino acid sequence, isoform 2 precursor (NP_001153392.1 GI:229892220; SEQ ID NO: 92)
```
   1    MVSYWDTGVL LCALLSCLLL TGSSSGSKLK DPELSLKGTQ HIMQAGQTLH LQCRGEAAHK

61    WSLPEMVSKE SERLSITKSA CGRNGKQFCS TLTLNTAQAN HTGFYSCKYL AVPTSKKKET

121    ESAIYIFISD TGRPFVEMYS EIPEIIHMTE GRELVIPCRV TSPNITVTLK KFPLDTLIPD

181    GKRIIWDSRK GFIISNATYK EIGLLTCEAT VNGHLYKTNY LTHRQTNTII DVQISTPRPV

241    KLLRGHTLVL NCTATTPLNT RVQMTWSYPD EKNKRASVRR RIDQSNSHAN IFYSVLTIDK

301    MQNKDKGLYT CRVRSGPSFK SVNTSVHIYD KAFITVKHRK QQVLETVAGK RSYRLSMKVK

361    AFPSPEVVWL KDGLPATEKS ARYLTRGYSL IIKDVTEEDA GNYTILLSIK QSNVFKNLTA

421    TLIVNVKPQI YEKAVSSFPD RALYPLGSRQ ILTCTAYGIP QPTIKWFWHP CNHNHSEARC

481    DFCSNNEESF ILDADSNMGN RIESITQRMA IIEGKNKMAS TLVVADSRIS GIYICIASNK

541    VGTVGRNISF YITDVPNGFH VNLEKMPTEG EDLKLSCTVN KFLYRDVTWI LLRTVNNRTM

601    HYSISKQKMA ITKEHSITLN LTIMNVSLQD SGTYACRARN VYTGEEILQK KEITIRGEHC

661    NKKAVFSRIS KFKSTRNDCT TQSNVKH
```

Human Flt-1 amino acid sequence, isoform 3 precursor (NP_001153502.1 GI:229892300; SEQ ID NO: 93)
```
   1    MVSYWDTGVL LCALLSCLLL TGSSSGSKLK DPELSLKGTQ HIMQAGQTLH LQCRGEAAHK

61    WSLPEMVSKE SERLSITKSA CGRNGKQFCS TLTLNTAQAN HTGFYSCKYL AVPTSKKKET

121    ESAIYIFISD TGRPFVEMYS EIPEIIHMTE GRELVIPCRV TSPNITVTLK KFPLDTLIPD

181    GKRIIWDSRK GFIISNATYK EIGLLTCEAT VNGHLYKTNY LTHRQTNTII DVQISTPRPV
```

TABLE 3 -continued

| | |
|---|---|
| 241 | KLLRGHTLVL NCTATTPLNT RVQMTWSYPD EKNKRASVRR RIDQSNSHAN IFYSVLTIDK |
| 301 | MQNKDKGLYT CRVRSGPSFK SVNTSVHIYD KAFITVKHRK QQVLETVAGK RSYRLSMKVK |
| 361 | AFPSPEVVWL KDGLPATEKS ARYLTRGYSL IIKDVTEEDA GNYTILLSIK QSNVFKNLTA |
| 421 | TLIVNVKPQI YEKAVSSFPD RALYPLGSRQ ILTCTAYGIP QPTIKWFWHP CNHNHSEARC |
| 481 | DFCSNNEESF ILDADSNMGN RIESITQRMA IIEGKNKMAS TLVVADSRIS GIYICIASNK |
| 541 | VGTVGRNISF YITDVPNGFH VNLEKMPTEG EDLKLSCTVN KFLYRDVTWI LLRTVNNRTM |
| 601 | HYSISKQKMA ITKEHSITLN LTIMNVSLQD SGTYACRARN VYTGEEILQK KEITIRDQEA |
| 661 | PYLLRNLSDH TVAISSSTTL DCHANGVPEP QITWFKNNHK IQQEPELYTS TSPSSSSSSP |
| 721 | LSSSSSSSSS SSS |

Human Flt-1 amino acid sequence, isoform 4 precursor (NP_001153503.1
GI:229892302; SEQ ID NO: 94)

| | |
|---|---|
| 1 | MVSYWDTGVL LCALLSCLLL TGSSSGSKLK DPELSLKGTQ HIMQAGQTLH LQCRGEAAHK |
| 61 | WSLPEMVSKE SERLSITKSA CGRNGKQFCS TLTLNTAQAN HTGFYSCKYL AVPTSKKKET |
| 121 | ESAIYIFISD TGRPFVEMYS EIPEIIHMTE GRELVIPCRV TSPNITVTLK KFPLDTLIPD |
| 181 | GKRIIWDSRK GFIISNATYK EIGLLTCEAT VNGHLYKTNY LTHRQTNTII DVQISTPRPV |
| 241 | KLLRGHTLVL NCTATTPLNT RVQMTWSYPD EKNKRASVRR RIDQSNSHAN IFYSVLTIDK |
| 301 | MQNKDKGLYT CRVRSGPSFK SVNTSVHIYD KAFITVKHRK QQVLETVAGK RSYRLSMKVK |
| 361 | AFPSPEVVWL KDGLPATEKS ARYLTRGYSL IIKDVTEEDA GNYTILLSIK QSNVFKNLTA |
| 421 | TLIVNVKPQI YEKAVSSFPD RALYPLGSRQ ILTCTAYGIP QPTIKWFWHP CNHNHSEARC |
| 481 | DFCSNNEESF ILDADSNMGN RIESITQRMA IIEGKNKLPP ANSSFMLPPT SFSSNYFHFL |
| 541 | P |

TABLE 4

| Fc Region Sequence (SEQ ID NO: 104) | |
|---|---|
| 209 | TKVDKKVEPK SCDKTHTCPP CPAPELLGGP SVFLFPPKPK DTLMISRTPE VTCVVVDVSH |
| 269 | EDPEVKFNWY VDGVEVHNAK TKPREEQYNS TYRVVSVLTV LHQDWLNGKE YKCKVSNKAL |
| 329 | PAPIEKTISK AKGQPREPQV YTLPPSREEM TKNQVSLTCL VKGFYPSDIA VEWESNGQPE |
| 389 | NNYKTTPPVL DSDGSFFLYS KLTVDKSRWQ QGNVFSCSVM HEALHNHYTQ KSLSLSPG |

We claim:

1. A method of treating bronchopulmonary dysplasia (BPD) in an infant comprising administering to an infant in need of treatment an effective amount of an anti-Flt-1 antibody or antigen fragment thereof, wherein the anti-Flt-1 antibody or antigen fragment thereof comprises:
a VL CDR1 defined by the amino acid sequence of SEQ ID NO: 21,
a VL CDR2 defined by the amino acid sequence of SEQ ID NO: 24,
a VL CDR3 defined by the amino acid sequence of SEQ ID NO: 32,
a HL CDR1 defined by the amino acid sequence of SEQ ID NO: 3,
a HL CDR2 defined by the amino acid sequence of SEQ ID NO: 12, and
a HL CDR3 defined by the amino acid sequence of SEQ ID NO: 17.

2. The method of claim 1, wherein the anti-Flt-1 antibody or antigen-binding fragment thereof is selected from the group consisting of IgG, F(ab')$_2$, F(ab)$_2$, Fab', Fab, ScFvs, diabodies, triabodies and tetrabodies.

3. The method of claim 1, wherein the anti-Flt-1 antibody or antigen-binding fragment thereof is a humanized monoclonal antibody.

4. The method of claim 3, wherein the humanized monoclonal antibody contains a human Fc region.

5. The method of claim 4, wherein the Fc region contains one or more mutations that enhance the binding affinity between the Fc region and the FcRn receptor such that the in vivo half-life of the antibody is prolonged.

6. The method of claim 5, wherein the Fc region contains one or more mutations at positions corresponding to Leu 234, Leu 235 and/or Gly 237 of human IgG1.

7. The method of claim 1, wherein the anti-Flt-1 antibody or antigen-binding fragment thereof does not bind to VEGFR2 and/or VEGFR3.

8. The method of claim 1, wherein the anti-Flt-1 antibody or antigen binding fragment thereof is administered parenterally.

9. The method of claim 8, wherein the parenteral administration is selected from intravenous, intradermal, intrathecal, inhalation, transdermal (topical), intraocular, intramuscular, subcutaneous, pulmonary delivery, and/or transmucosal administration.

10. The method of claim 1, wherein the anti-Flt-1 antibody or antigen binding fragment thereof is administered bimonthly, monthly, triweekly, biweekly, weekly, daily, or at variable intervals.

11. The method of claim 1, wherein the anti-Flt-1 antibody or antigen binding fragment thereof is delivered to one or more target tissues selected from lungs and heart.

12. The method of claim 1, wherein the administration of the anti-Flt-1 antibody or antigen binding fragment thereof results in growth of healthy lung tissue, decreased lung inflammation, increased alveologenesis, increased angiogenesis, improved structure of pulmonary vascular bed, reduced lung scarring, improved lung growth, reduced respiratory insufficiency, improved exercise tolerance, reduced adverse neurological outcome, and/or improved pulmonary function relative to a control.

13. The method of claim 1, further comprising co-administering at least one additional agent or therapy selected from a surfactant, oxygen therapy, ventilator therapy, a steroid, vitamin A, inhaled nitric oxide, high calorie nutritional formulation, a diuretic, and/or a bronchodilator.

14. The method of claim 1, wherein the anti-Flt-1 antibody or antigen fragment thereof comprises:
(a) a light chain variable (VL) region comprising an amino acid sequence having at least 90% identity to SEQ ID NO: 60 and a heavy chain variable (VH) region comprising an amino acid sequence having at least 90% identity to SEQ ID NO: 45; or
(b) a light chain comprising an amino acid sequence having at least 90% identity with SEQ ID NO: 76 and a heavy chain comprising an amino acid sequence having at least 90% identity with SEQ ID NO: 71.

15. An anti-Flt-1 antibody or antigen fragment thereof, wherein the anti-Flt-1 antibody or antigen-binding fragment thereof comprises:
a VL CDR1 defined by an amino acid sequence of SEQ ID NO:21,
a VL CDR2 defined by an amino acid sequence of SEQ ID NO:24,
a VL CDR3 defined by an amino acid sequence of SEQ ID NO:32,
a VH CDR1 defined by an amino acid sequence of SEQ ID NO: 3,
a VH CDR2 defined by an amino acid sequence of SEQ ID NO:12, and
a VH CDR3 defined by an amino acid sequence of SEQ ID NO:17.

16. The anti-Flt-1 antibody or antigen fragment thereof of claim 15, wherein the anti-Flt-1 antibody or antigen fragment thereof comprises:
(a) a light chain variable (VL) region comprising an amino acid sequence having at least 90% identity to SEQ ID NO: 60 and a heavy chain variable (VH) region comprising an amino acid sequence having at least 90% identity to SEQ ID NO: 45; or
(b) a light chain comprising an amino acid sequence having at least 90% identity with SEQ ID NO: 76 and a heavy chain comprising an amino acid sequence having at least 90% identity with SEQ ID NO: 71.

* * * * *

SEQUENCE LISTING

```
<160> NUMBER OF SEQ ID NOS: 111

<210> SEQ ID NO 1
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 1

Ser Tyr Ala Met Ser
1               5

<210> SEQ ID NO 2
<211> LENGTH: 5
```

```
<212> TYPE: PRT
<213> ORGANISM: Artificial Sequence
<220> FEATURE:
<223> OTHER INFORMATION: Synthetic Oligopeptide

<400> SEQUENCE: 2

Asp Tyr Ser Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 3

Asp Tyr Ser Ala Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic oligopeptide

<400> SEQUENCE: 4

Asp Tyr Ser Leu Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 5

Ala Ile Ser Gly Ser Gly Gly Ser Thr Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 6

Ala Ile Ser Trp Asn Gly Asp Ser Thr Tyr Tyr Ala Glu Ser Met Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 7

Ala Ile Ser Trp Asn Gly Asp Ser Thr Tyr Tyr Ala Glu Ser Leu Lys
1               5                   10                  15
```

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 8

Ala Ile Ser Trp Asn Gly Asp Ser Thr Tyr Tyr Ala Glu Ser Ala Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic Oligpeptide

<400> SEQUENCE: 9

Ala Ile Ser Trp Asn Gly Asp Ser Thr Tyr Tyr Ala Glu Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 10

Ala Ile Thr Trp Ser Gly Asp Ser Thr Tyr Tyr Ala Glu Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 11

Ala Ile Ser Trp Ser Gly Asp Ser Thr Tyr Tyr Ala Glu Ser Leu Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synethic oligopeptide

<400> SEQUENCE: 12

Ala Ile Ser Trp Ser Gly Asp Ser Thr Tyr Tyr Ala Glu Ser Val Lys
1               5                   10                  15

Gly

<210> SEQ ID NO 13

```
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 13

Ala Ile Ser Trp Gln Gly Asp Ser Thr Tyr Tyr Ala Glu Ser Ala Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 14

Ala Ile Ser Trp Asn Ala Asp Ser Thr Tyr Tyr Ala Glu Ser Ala Lys
1               5                   10                  15

Gly

<210> SEQ ID NO 15
<211> LENGTH: 2
<212> TYPE: PRT
<213> ORGANISM: Artificial Sequence
<220> FEATURE:
<223> OTHER INFORMATION: Synthetic Oligopeptide

<400> SEQUENCE: 15

Asp Tyr
1

<210> SEQ ID NO 16
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 16

Ser Trp Ala Thr Pro Ile Glu Ser Leu Tyr Tyr Tyr Gly Met Asp Tyr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 17

Ser Trp Ala Thr Pro Ile Glu Ser Leu Tyr Tyr Tyr Gly Ser Asp Tyr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 18

Ser Trp Ala Thr Pro Ile Glu Ser Leu Tyr Tyr Tyr Gly Thr Asp Tyr
1               5                   10                  15
```

```
<210> SEQ ID NO 19
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 19

Gly Gly Asn Asn Ile Gly Ser Lys Asn Val His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 20

Gly Gly Asn Asn Leu Gly Tyr Lys Ser Val His
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Sythetic Oligopeptide

<400> SEQUENCE: 21

Gly Gly Asn Asn Ile Gly Ser Gln Thr Ala Gln
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 22

Arg Asp Ser Asn Arg Pro Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 23

Arg Asp Asn Asn Arg Pro Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 24

Ala Asn Asn Arg Arg Pro Ser
1               5
```

```
<210> SEQ ID NO 25
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 25

Gln Val Val Val
1

<210> SEQ ID NO 26
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 26

Gln Val Trp Asp Gly Ser Thr Gln Ala Ile Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 27

Gln Val Trp Glu Asp Ser Thr Gln Ala Ile Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 28

Gln Val Trp Asp Glu Ser Thr Gln Ala Ile Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 29

Gln Val Trp Ala Ala Ser Thr Gln Ala Ile Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 30

Gln Val Trp Asp Asp Ser Thr Gln Ala Ile Val
1               5                   10
```

```
<210> SEQ ID NO 31
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 31

Gln Val Trp Glu Ala Ser Thr Gln Ala Ile Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 32

Gln Val Trp Asp Ala Ser Thr Gln Ala Ile Val
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 33

Gln Val Trp Glu Glu Ser Thr Gln Ala Ile Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 34

Gln Val Trp Glu Gly Ser Thr Gln Ala Ile Val
1               5                   10

<210> SEQ ID NO 35
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Asp Tyr Trp Gly Gln Gly Thr Leu Val Thr Val Ser Ser
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Trp Gly Gln Gly Thr Leu Val Thr Val Ser Ser
            100                 105                 110

<210> SEQ ID NO 37
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 37

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Trp Ala Thr Pro Ile Glu Ser Leu Tyr Tyr Tyr Gly Met
            100                 105                 110

Asp Tyr Trp Gly Lys Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 38

Glu Leu Gln Leu Val Glu Ser Gly Gly Gly Leu Val Gln Pro Gly Gly

```
                1               5                  10                 15
            Ser Leu Arg Leu Ser Cys Ala Ala Ser Gly Phe Thr Phe Arg Asp Tyr
                        20                  25                 30

Ser Met Ser Trp Val Arg Gln Ala Pro Gly Lys Gly Leu Glu Trp Val
                        35                  40                 45

Ser Ala Ile Ser Trp Asn Gly Asp Ser Thr Tyr Tyr Ala Glu Ser Leu
                        50                  55                 60

Lys Gly Arg Phe Thr Ile Ser Arg Asp Asn Ala Lys Asn Thr Leu Tyr
             65                  70                  75                 80

Leu Gln Met Asn Ser Leu Arg Ala Glu Asp Thr Ala Val Tyr Tyr Cys
                        85                  90                 95

Ala Lys Ser Trp Ala Thr Pro Ile Glu Ser Leu Tyr Tyr Gly Ser
                        100                 105                110

Asp Tyr Trp Gly Gln Gly Thr Leu Val Thr Val Ser Ser
                        115                 120                125
```

<210> SEQ ID NO 39
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 39

```
            Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Arg Asp Tyr
                        20                  25                 30

Ser Met Ser Trp Val Arg Gln Ala Pro Gly Lys Gly Leu Glu Trp Val
                        35                  40                 45

Ser Ala Ile Ser Trp Asn Gly Asp Ser Thr Tyr Tyr Ala Glu Ser Ala
                        50                  55                 60

Lys Gly Arg Phe Thr Ile Ser Arg Asp Asn Ser Lys Asn Thr Leu Tyr
             65                  70                  75                 80

Leu Gln Met Asn Ser Leu Arg Ala Glu Asp Thr Ala Val Tyr Tyr Cys
                        85                  90                 95

Ala Lys Ser Trp Ala Thr Pro Ile Glu Ser Leu Tyr Tyr Gly Ser
                        100                 105                110

Asp Tyr Trp Gly Gln Gly Thr Leu Val Thr Val Ser Ser
                        115                 120                125
```

<210> SEQ ID NO 40
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 40

```
            Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Arg Asp Tyr
                        20                  25                 30

Ser Ala Ser Trp Val Arg Gln Ala Pro Gly Lys Gly Leu Glu Trp Val
                        35                  40                 45

Ser Ala Ile Ser Trp Asn Gly Asp Ser Thr Tyr Tyr Ala Glu Ser Val
                        50                  55                 60
```

```
Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
            115                 120                 125

<210> SEQ ID NO 41
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
                20                  25                  30

Ser Met Ser Trp Val Arg Gln Ala Pro Gly Lys Gly Leu Glu Trp Val
            35                  40                  45

Ser Ala Ile Thr Trp Ser Gly Asp Ser Thr Tyr Tyr Ala Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Thr
            100                 105                 110

Asp Tyr Trp Gly Lys Gly Thr Leu Val Thr Val Ser Ser
            115                 120                 125

<210> SEQ ID NO 42
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
                20                  25                  30

Ser Met Ser Trp Val Arg Gln Ala Pro Gly Lys Gly Leu Glu Trp Val
            35                  40                  45

Ser Ala Ile Ser Trp Asn Gly Asp Ser Thr Tyr Tyr Ala Glu Ser Ala
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
            115                 120                 125
```

```
<210> SEQ ID NO 43
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 43
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Leu Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Lys Gly Thr Leu Val Thr Val Ser Ser
        115                 120                 125

```
<210> SEQ ID NO 44
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 44
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Lys Gly Thr Leu Val Thr Val Ser Ser
        115                 120                 125

```
<210> SEQ ID NO 45
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 45
```

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Tyr Tyr Tyr Gly Ser
            100                 105                 110

Asp Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Tyr Tyr Tyr Gly Ser
            100                 105                 110

Asp Tyr Trp Gly Gln Gly Thr Leu Val Thr Val Ser Ser
        115                 120                 125

<210> SEQ ID NO 47
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Asp Tyr
             20                  25                  30

Ser Met Ser Trp Val Arg Gln Ala Pro Gly Lys Gly Leu Glu Trp Val
         35                  40                  45

Ser Ala Ile Ser Trp Asn Ala Asp Ser Thr Tyr Tyr Ala Glu Ser Ala
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 49
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 49

Ser Tyr Glu Leu Thr Gln Pro Leu Ser Val Ser Val Ala Leu Gly Gln
 1               5                  10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Ile Tyr
         35                  40                  45

Arg Asp Ser Asn Arg Pro Ser Gly Ile Pro Glu Arg Phe Ser Gly Ser
     50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Val Val Phe Gly Gly Gly Thr
                 85                  90                  95

Lys Leu Thr Val Leu
            100
```

<210> SEQ ID NO 50
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 50

```
Ser Tyr Glu Leu Thr Gln Pro Leu Ser Val Ser Val Ala Leu Gly Gln
1               5                   10                  15

Ala Ala Arg Ile Thr Cys Gly Gly Asn Asn Leu Gly Tyr Lys Ser Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Val Phe Gly Gly Gly Thr
                85                  90                  95

Lys Leu Thr Val Leu
            100
```

<210> SEQ ID NO 51
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 51

```
Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Gly Ala Gln Ala Glu
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr His Leu Thr Val Leu
            100                 105
```

<210> SEQ ID NO 52
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 52

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45
```

Ala Asn Asn Arg Arg Pro Ser Gly Ile Pro Glu Arg Phe Ser Gly Ser
        50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Glu Asp Ser Thr Gln Ala
                 85                  90                  95

Ile Val Phe Gly Gly Gly Thr Lys Leu Thr Val Leu
            100                 105

<210> SEQ ID NO 53
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 53

Ser Tyr Glu Leu Thr Gln Pro Leu Ser Val Ser Val Ala Leu Arg Gln
 1                   5                  10                  15

Thr Ala Arg Ile Thr Cys Gly Gly Asn Asn Ile Gly Ser Gln Thr Ala
                20                  25                  30

Gln Trp Tyr Gln Gln Lys Pro Gly Gln Ala Pro Val Leu Val Ile Tyr
            35                  40                  45

Ala Asn Asn Arg Arg Pro Ser Gly Ile Pro Glu Arg Phe Ser Gly Ser
        50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Asp Glu Ser Thr Gln Ala
                 85                  90                  95

Ile Val Phe Gly Gly Gly Thr Lys Leu Thr Val Leu
            100                 105

<210> SEQ ID NO 54
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 54

Ser Tyr Glu Leu Thr Gln Pro Leu Ser Val Ser Val Ala Leu Gly Gln
 1                   5                  10                  15

Thr Ala Arg Ile Thr Cys Gly Gly Asn Asn Ile Gly Ser Gln Thr Ala
                20                  25                  30

Gln Trp Tyr Gln Gln Lys Pro Gly Gln Ala Pro Val Leu Val Ile Tyr
            35                  40                  45

Ala Asn Asn Arg Arg Pro Ser Gly Ile Pro Glu Arg Phe Ser Gly Ser
        50                  55                  60

Lys Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Ala Ala Ser Thr Gln Ala
                 85                  90                  95

Ile Val Phe Gly Gly Gly Thr Lys Leu Thr Val Leu
            100                 105

<210> SEQ ID NO 55
<211> LENGTH: 108
<212> TYPE: PRT

<213> ORGANISM: Artificial Sequence
<220> FEATURE:
<223> OTHER INFORMATION: Synthetic Polypeptide

<400> SEQUENCE: 55

```
Ser Tyr Glu Leu Thr Gln Pro Leu Ser Val Ser Val Ala Leu Arg Gln
1               5                   10                  15

Ala Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Asp Ser Thr Gln Ala
                85                  90                  95

Ile Val Phe Gly Gly Gly Thr Lys Leu Thr Val Leu
            100                 105
```

<210> SEQ ID NO 56
<211> LENGTH: 108
<212> TYPE: PRT
<213> ORGANISM: Artificial Sequence
<220> FEATURE:
<223> OTHER INFORMATION: Synthetic Oligopeptide

<400> SEQUENCE: 56

```
Ser Tyr Glu Leu Thr Gln Pro Leu Ser Val Ser Val Ala Leu Arg Gln
1               5                   10                  15

Ala Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Ala Ser Thr Gln Ala
                85                  90                  95

Ile Val Phe Gly Gly Gly Thr Lys Leu Thr Val Leu
            100                 105
```

<210> SEQ ID NO 57
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 57

```
Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60
```

```
Lys Ser Gly Asn Thr Ala Thr Leu Thr Ile Ser Gly Ala Gln Ala Gly
 65                  70                  75                  80

Asp Glu Ala Asp Tyr Tyr Cys Gln Val Trp Asp Ala Ser Thr Gln Ala
                 85                  90                  95

Ile Val Phe Gly Gly Gly Thr Lys Leu Thr Val Leu
            100                 105

<210> SEQ ID NO 58
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 58

Ser Tyr Glu Leu Thr Gln Pro Leu Ser Val Ser Val Ala Leu Gly Gln
 1               5                  10                  15

Thr Ala Lys Ile Thr Cys Gly Gly Asn Asn Ile Gly Ser Gln Thr Ala
                 20                  25                  30

Gln Trp Tyr Gln Gln Lys Pro Gly Gln Ala Pro Val Leu Val Ile Tyr
             35                  40                  45

Ala Asn Asn Arg Arg Pro Ser Gly Ile Pro Glu Arg Phe Ser Gly Ser
     50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Glu Glu Ser Thr Gln Ala
                 85                  90                  95

Ile Val Phe Gly Gly Gly Thr His Leu Thr Val Leu
            100                 105

<210> SEQ ID NO 59
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 59

Ser Tyr Glu Leu Thr Gln Pro Leu Ser Val Ser Val Ala Leu Arg Gln
 1               5                  10                  15

Ala Ala Lys Ile Thr Cys Gly Gly Asn Asn Ile Gly Ser Gln Thr Ala
                 20                  25                  30

Gln Trp Tyr Gln Gln Lys Pro Gly Gln Ala Pro Val Leu Val Ile Tyr
             35                  40                  45

Ala Asn Asn Arg Arg Pro Ser Gly Ile Pro Glu Arg Phe Ser Gly Ser
     50                  55                  60

Lys Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Gly Ser Thr Gln Ala
                 85                  90                  95

Ile Val Phe Gly Gly Gly Thr Lys Leu Thr Val Leu
            100                 105

<210> SEQ ID NO 60
<211> LENGTH: 108
<212> TYPE: PRT
<213> ORGANISM: Artificial Sequence
<220> FEATURE:
<223> OTHER INFORMATION: Synthetic Polypeptide
```

<400> SEQUENCE: 60

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ala Ser Thr Gln Ala
                85                  90                  95

Ile Val Phe Gly Gly Gly Thr Lys Leu Thr Val Leu
            100                 105

<210> SEQ ID NO 61
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 61

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Glu Gly Ser Thr Gln Ala
                85                  90                  95

Ile Val Phe Gly Gly Gly Thr Lys Leu Thr Val Leu
            100                 105

<210> SEQ ID NO 62
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 62

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95
Ala Lys Ser Trp Ala Thr Pro Ile Glu Ser Leu Tyr Tyr Gly Ser
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 63
<211> LENGTH: 455
<212> TYPE: PRT
<213> ORGANISM: Artificial Sequence
<220> FEATURE:
```

<223> OTHER INFORMATION: Synthetic Polypeptide

<400> SEQUENCE: 63

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400
```

```
Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 64
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 65
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

```
Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 66
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 66

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110
```

```
Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 67
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 67

Glu Leu Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser

-continued

```
                435                 440                 445
Leu Ser Leu Ser Pro Gly Lys
    450                 455

<210> SEQ ID NO 68
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 68

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
```

```
                    340                 345                 350
Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
        450                 455

<210> SEQ ID NO 69
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Pro Lys Pro Lys
```

Asp Thr Leu Met Ile Ser Arg Thr Pro Glu Val Thr Cys Val Val Val
            245                 250                 255
Asp Val Ser His Glu Asp Pro Glu Val Lys Phe Asn Trp Tyr Val Asp
        260                 265                 270
Gly Val Glu Val His Asn Ala Lys Thr Lys Pro Arg Glu Glu Gln Tyr
    275                 280                 285
Asn Ser Thr Tyr Arg Val Val Ser Val Leu Thr Val Leu His Gln Asp
290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Pro Arg
            325                 330                 335
Glu Pro Gln Val Tyr Thr Leu Pro Pro Ser Arg Asp Glu Leu Thr Lys
        340                 345                 350
Asn Gln Val Ser Leu Thr Cys Leu Val Lys Gly Phe Tyr Pro Ser Asp
    355                 360                 365
Ile Ala Val Glu Trp Glu Ser Asn Gly Gln Pro Glu Asn Asn Tyr Lys
370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
            405                 410                 415
Cys Ser Val Met His Glu Ala Leu His Asn His Tyr Thr Gln Lys Ser
        420                 425                 430
Leu Ser Leu Ser Pro Gly Lys
    435                 440

<210> SEQ ID NO 70
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 70

Glu Leu Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Asp Tyr
            20                  25                  30
Ser Met Ser Trp Val Arg Gln Ala Pro Gly Lys Gly Leu Glu Trp Val
        35                  40                  45
Ser Ala Ile Ser Trp Asn Gly Asp Ser Thr Tyr Tyr Ala Glu Ser Met
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Ser Glu Asp Thr Ala Val Tyr Tyr Cys
            85                  90                  95
Ala Lys Ser Trp Ala Thr Pro Ile Glu Ser Leu Tyr Tyr Tyr Gly Met
        100                 105                 110
Asp Tyr Trp Gly Lys Gly Thr Leu Val Thr Val Ser Ser Ala Ser Thr
    115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu

```
            145                 150                 155                 160
    Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                    180                 185                 190

Val Val Thr Val Pro Ser Ser Leu Gly Thr Gln Thr Tyr Ile Cys
                    195                 200                 205

Asn Val Asn His Lys Pro Ser Asn Thr Lys Val Asp Lys Lys Val Glu
                    210                 215                 220

Pro Lys Ser Cys Asp Lys Thr His Thr Cys Pro Pro Cys Pro Ala Pro
    225                 230                 235                 240

Glu Ala Ala Gly Ala Pro Ser Val Phe Leu Phe Pro Pro Lys Pro Lys
                    245                 250                 255

Asp Thr Leu Met Ile Ser Arg Thr Pro Glu Val Thr Cys Val Val Val
                    260                 265                 270

Asp Val Ser His Glu Asp Pro Glu Val Lys Phe Asn Trp Tyr Val Asp
                    275                 280                 285

Gly Val Glu Val His Asn Ala Lys Thr Lys Pro Arg Glu Glu Gln Tyr
                    290                 295                 300

Asn Ser Thr Tyr Arg Val Val Ser Val Leu Thr Val Leu His Gln Asp
    305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                    340                 345                 350

Glu Pro Gln Val Tyr Thr Leu Pro Pro Ser Arg Asp Glu Leu Thr Lys
                    355                 360                 365

Asn Gln Val Ser Leu Thr Cys Leu Val Lys Gly Phe Tyr Pro Ser Asp
                    370                 375                 380

Ile Ala Val Glu Trp Glu Ser Asn Gly Gln Pro Glu Asn Asn Tyr Lys
    385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                    420                 425                 430

Cys Ser Val Met His Glu Ala Leu His Asn His Tyr Thr Gln Lys Ser
                    435                 440                 445

Leu Ser Leu Ser Pro Gly Lys
        450                 455

<210> SEQ ID NO 71
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 71

Glu Leu Gln Leu Val Glu Ser Gly Gly Gly Leu Val Gln Pro Gly Gly
    1               5                   10                  15

Ser Leu Arg Leu Ser Cys Ala Ala Ser Gly Phe Thr Phe Ser Asp Tyr
                    20                  25                  30

Ser Ala Ser Trp Val Arg Gln Ala Pro Gly Lys Gly Leu Glu Trp Val
                    35                  40                  45

Ser Ala Ile Ser Trp Ser Gly Asp Ser Thr Tyr Tyr Ala Glu Ser Val
```

-continued

```
                 50                  55                  60
Lys Gly Arg Phe Thr Ile Phe Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ser Trp Ala Thr Pro Ile Glu Ser Leu Tyr Tyr Gly Ser
                100                 105                 110
Asp Tyr Trp Gly Gln Gly Thr Leu Val Thr Val Ser Ser Ala Ser Thr
                115                 120                 125
Lys Gly Pro Ser Val Phe Pro Leu Ala Pro Ser Ser Lys Ser Thr Ser
                130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
Val Val Thr Val Pro Ser Ser Ser Leu Gly Thr Gln Thr Tyr Ile Cys
                195                 200                 205
Asn Val Asn His Lys Pro Ser Asn Thr Lys Val Asp Lys Lys Val Glu
                210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
                260                 265                 270
Asp Val Ser His Glu Asp Pro Glu Val Lys Phe Asn Trp Tyr Val Asp
                275                 280                 285
Gly Val Glu Val His Asn Ala Lys Thr Lys Pro Arg Glu Glu Gln Tyr
                290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Asp Glu Leu Thr Lys
                355                 360                 365
Asn Gln Val Ser Leu Thr Cys Leu Val Lys Gly Phe Tyr Pro Ser Asp
                370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys
                450                 455

<210> SEQ ID NO 72
```

<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 72

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380
```

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 73
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

```
Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 74
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 74

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Trp Ala Thr Pro Ile Glu Ser Leu Tyr Tyr Tyr Gly Met
            100                 105                 110

Asp Tyr Trp Gly Lys Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Ser Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met Asn Glu Ala Leu His Asn His Tyr Thr Gln Lys Ser
        435                 440                 445

Leu Ser Leu Ser Pro Gly Lys
    450                 455

<210> SEQ ID NO 75
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 75

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Glu Gly Ser Thr Gln Ala
                85                  90                  95
```

```
Ile Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 76
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 76

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ala Ser Thr Gln Ala
                85                  90                  95

Ile Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 77
```

```
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 77

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Glu Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 78
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 78

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Glu Ser Thr Gln Ala
                85                  90                  95

Ile Val Phe Gly Gly Gly Thr Lys Leu Thr Val Leu Gly Gln Pro Lys
```

```
                100             105             110
Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 79
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 79

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 80
<211> LENGTH: 214
<212> TYPE: PRT

<213> ORGANISM: Artificial Sequence
<220> FEATURE:
<223> OTHER INFORMATION: Synthetic Polypeptide

<400> SEQUENCE: 80

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 81
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 81

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Asp Ser Thr Gln Ala
                85                  90                  95

Ile Val Phe Gly Gly Gly Thr Lys Leu Thr Val Leu Gly Gln Pro Lys
            100                 105                 110
```

```
Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 82
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 82

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 83
<211> LENGTH: 214
<212> TYPE: PRT
<213> ORGANISM: Artificial Sequence
<220> FEATURE:
```

<223> OTHER INFORMATION: Synthetic Polypeptide

<400> SEQUENCE: 83

```
Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Gly Ala Gln Ala Glu
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr His Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 84
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 84

```
Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125
```

```
Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 85
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 85

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 86
<211> LENGTH: 214
<212> TYPE: PRT
<213> ORGANISM: Artificial Sequence
<220> FEATURE:
<223> OTHER INFORMATION: Synthetic Polypeptide
```

<400> SEQUENCE: 86

```
Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 87
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 87

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
            165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 89
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Ser Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met Asn Glu Ala Leu His Asn His Tyr Thr
305                 310                 315                 320

Gln Lys Ser Leu Ser Leu Ser Pro Gly Lys
                325                 330

<210> SEQ ID NO 90
<211> LENGTH: 1338
<212> TYPE: PRT
<213> ORGANISM: Homo sapiens

<400> SEQUENCE: 90

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

```
Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
        610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
```

-continued

```
                 660                 665                 670
Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
        770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
        850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
        930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
        1010                1015                1020

Ala Ala Arg Asn Ile Leu Leu Ser Glu Asn Asn Val Val Lys Ile
        1025                1030                1035

Cys Asp Phe Gly Leu Ala Arg Asp Ile Tyr Lys Asn Pro Asp Tyr
        1040                1045                1050

Val Arg Lys Gly Asp Thr Arg Leu Pro Leu Lys Trp Met Ala Pro
        1055                1060                1065

Glu Ser Ile Phe Asp Lys Ile Tyr Ser Thr Lys Ser Asp Val Trp
        1070                1075                1080
```

```
Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 91
<211> LENGTH: 720
<212> TYPE: PRT
<213> ORGANISM: Homo sapiens

<400> SEQUENCE: 91

Met Val Ser Tyr Trp Asp Thr Gly Val Leu Leu Cys Ala Leu Leu
1               5                   10                  15

Cys Leu Leu Leu Thr Gly Ser Ser Gly Ser Lys Leu Lys Asp Pro
                20                  25                  30

Glu Leu Ser Leu Lys Gly Thr Gln His Ile Met Gln Ala Gly Gln
            35                  40                  45

Leu His Leu Gln Cys Arg Gly Glu Ala Ala His Lys Trp Ser Leu
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
```

```
                100                 105                 110
Pro Thr Ser Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
            130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
            370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525
```

```
Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
        610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
        690                 695                 700

Pro Asp Ala Asp Pro His Ile Gln Lys Ala Asp Cys Thr Phe Phe Phe
705                 710                 715                 720

<210> SEQ ID NO 92
<211> LENGTH: 687
<212> TYPE: PRT
<213> ORGANISM: Homo sapiens

<400> SEQUENCE: 92

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
```

```
                180             185             190
Ile Ile Ser Asn Ala Thr Tyr Lys Glu Ile Gly Leu Leu Thr Cys Glu
            195                 200             205

Ala Thr Val Asn Gly His Leu Tyr Lys Thr Asn Tyr Leu Thr His Arg
        210                 215             220

Gln Thr Asn Thr Ile Ile Asp Val Gln Ile Ser Thr Pro Arg Pro Val
225                     230              235               240

Lys Leu Leu Arg Gly His Thr Leu Val Leu Asn Cys Thr Ala Thr Thr
                245                 250             255

Pro Leu Asn Thr Arg Val Gln Met Thr Trp Ser Tyr Pro Asp Glu Lys
            260                 265             270

Asn Lys Arg Ala Ser Val Arg Arg Ile Asp Gln Ser Asn Ser His
        275                 280             285

Ala Asn Ile Phe Tyr Ser Val Leu Thr Ile Asp Lys Met Gln Asn Lys
        290                 295             300

Asp Lys Gly Leu Tyr Thr Cys Arg Val Arg Ser Gly Pro Ser Phe Lys
305                 310                 315             320

Ser Val Asn Thr Ser Val His Ile Tyr Asp Lys Ala Phe Ile Thr Val
                325                 330             335

Lys His Arg Lys Gln Gln Val Leu Glu Thr Val Ala Gly Lys Arg Ser
            340                 345             350

Tyr Arg Leu Ser Met Lys Val Lys Ala Phe Pro Ser Pro Glu Val Val
        355                 360             365

Trp Leu Lys Asp Gly Leu Pro Ala Thr Glu Lys Ser Ala Arg Tyr Leu
        370                 375             380

Thr Arg Gly Tyr Ser Leu Ile Ile Lys Asp Val Thr Glu Glu Asp Ala
385                 390                 395             400

Gly Asn Tyr Thr Ile Leu Leu Ser Ile Lys Gln Ser Asn Val Phe Lys
                405                 410             415

Asn Leu Thr Ala Thr Leu Ile Val Asn Val Lys Pro Gln Ile Tyr Glu
            420                 425             430

Lys Ala Val Ser Ser Phe Pro Asp Pro Ala Leu Tyr Pro Leu Gly Ser
        435                 440             445

Arg Gln Ile Leu Thr Cys Thr Ala Tyr Gly Ile Pro Gln Pro Thr Ile
        450                 455             460

Lys Trp Phe Trp His Pro Cys Asn His Asn His Ser Glu Ala Arg Cys
465                 470                 475             480

Asp Phe Cys Ser Asn Asn Glu Glu Ser Phe Ile Leu Asp Ala Asp Ser
                485                 490             495

Asn Met Gly Asn Arg Ile Glu Ser Ile Thr Gln Arg Met Ala Ile Ile
            500                 505             510

Glu Gly Lys Asn Lys Met Ala Ser Thr Leu Val Val Ala Asp Ser Arg
        515                 520             525

Ile Ser Gly Ile Tyr Ile Cys Ile Ala Ser Asn Lys Val Gly Thr Val
        530                 535             540

Gly Arg Asn Ile Ser Phe Tyr Ile Thr Asp Val Pro Asn Gly Phe His
545                 550                 555             560

Val Asn Leu Glu Lys Met Pro Thr Glu Gly Glu Asp Leu Lys Leu Ser
                565                 570             575

Cys Thr Val Asn Lys Phe Leu Tyr Arg Asp Val Thr Trp Ile Leu Leu
            580                 585             590

Arg Thr Val Asn Asn Arg Thr Met His Tyr Ser Ile Ser Lys Gln Lys
        595                 600             605
```

```
Met Ala Ile Thr Lys Glu His Ser Ile Thr Leu Asn Leu Thr Ile Met
            610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Gly Glu His Cys Asn Lys Lys Ala Val Phe Ser Arg Ile Ser Lys Phe
                660                 665                 670
Lys Ser Thr Arg Asn Asp Cys Thr Thr Gln Ser Asn Val Lys His
                675                 680                 685

<210> SEQ ID NO 93
<211> LENGTH: 733
<212> TYPE: PRT
<213> ORGANISM: Homo sapiens

<400> SEQUENCE: 93

Met Val Ser Tyr Trp Asp Thr Gly Val Leu Leu Cys Ala Leu Leu Ser
1               5                   10                  15
Cys Leu Leu Leu Thr Gly Ser Ser Ser Gly Ser Lys Leu Lys Asp Pro
                20                  25                  30
Glu Leu Ser Leu Lys Gly Thr Gln His Ile Met Gln Ala Gly Gln Thr
            35                  40                  45
Leu His Leu Gln Cys Arg Gly Glu Ala Ala His Lys Trp Ser Leu Pro
        50                  55                  60
Glu Met Val Ser Lys Glu Ser Glu Arg Leu Ser Ile Thr Lys Ser Ala
65                  70                  75                  80
Cys Gly Arg Asn Gly Lys Gln Phe Cys Ser Thr Leu Thr Leu Asn Thr
                85                  90                  95
Ala Gln Ala Asn His Thr Gly Phe Tyr Ser Cys Lys Tyr Leu Ala Val
                100                 105                 110
Pro Thr Ser Lys Lys Lys Glu Thr Glu Ser Ala Ile Tyr Ile Phe Ile
            115                 120                 125
Ser Asp Thr Gly Arg Pro Phe Val Glu Met Tyr Ser Glu Ile Pro Glu
130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
```

-continued

```
            290                 295                 300
Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
                435                 440                 445

Arg Gln Ile Leu Thr Cys Thr Ala Tyr Gly Ile Pro Gln Pro Thr Ile
                450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
                515                 520                 525

Ile Ser Gly Ile Tyr Ile Cys Ile Ala Ser Asn Lys Val Gly Thr Val
                530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
        610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
                675                 680                 685

Glu Pro Gln Ile Thr Trp Phe Lys Asn Asn His Lys Ile Gln Gln Glu
                690                 695                 700

Pro Glu Leu Tyr Thr Ser Thr Ser Pro Ser Ser Ser Ser Ser Ser Pro
705                 710                 715                 720
```

Leu Ser Ser Ser Ser Ser Ser Ser Ser Ser Ser
            725                 730

<210> SEQ ID NO 94
<211> LENGTH: 541
<212> TYPE: PRT
<213> ORGANISM: Homo sapiens

<400> SEQUENCE: 94

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val

```
                355                 360                 365
Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
        515                 520                 525

Pro Thr Ser Phe Ser Ser Asn Tyr Phe His Phe Leu Pro
    530                 535                 540

<210> SEQ ID NO 95
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 95

Glu Ile Pro Glu Ile Ile His Met Thr Glu Gly Arg Glu
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Oligopeptide

<400> SEQUENCE: 96

Ile Ile Ser Asn Ala Thr Tyr Lys Glu Ile Gly Leu Leu Thr
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 97

Asp Thr Gly Arg Pro Phe Val Glu Met
1               5

<210> SEQ ID NO 98
<211> LENGTH: 8
<212> TYPE: PRT
<213> ORGANISM: Artificial Sequence
```

```
<220> FEATURE:
<223> OTHER INFORMATION: Synthetic Oligopeptide

<400> SEQUENCE: 98

Glu Ile Pro Glu Ile Ile His Met
1               5

<210> SEQ ID NO 99
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 99

Tyr Ser Glu Ile Pro Glu Ile Ile His Met
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic Oligopeptide

<400> SEQUENCE: 100

Tyr Ser Glu Ile Pro Glu Ile Ile His Met Thr Glu Gly Arg Glu
1               5                   10                  15

<210> SEQ ID NO 101
<211> LENGTH: 29
<212> TYPE: PRT
<213> ORGANISM: Artificial Sequence
<220> FEATURE:
<223> OTHER INFORMATION: Synthetic Oligopeptide

<400> SEQUENCE: 101

Ile Pro Asp Gly Lys Arg Ile Ile Trp Asp Ser Arg Lys Gly Phe Ile
1               5                   10                  15

Ile Ser Asn Ala Thr Tyr Lys Glu Ile Gly Leu Leu Thr
            20                  25

<210> SEQ ID NO 102
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 102

Tyr Lys Glu Ile Gly Leu
1               5

<210> SEQ ID NO 103
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 103

Ile Ser Asp Thr Gly Arg Pro Phe Val Glu Met
1               5                   10

<210> SEQ ID NO 104
<211> LENGTH: 238
```

<212> TYPE: PRT
<213> ORGANISM: Artificial Sequence
<220> FEATURE:
<223> OTHER INFORMATION: Synthetic Polypeptide

<400> SEQUENCE: 104

Thr Lys Val Asp Lys Lys Val Glu Pro Lys Ser Cys Asp Lys Thr His
1               5                   10                  15

Thr Cys Pro Pro Cys Pro Ala Pro Glu Leu Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly
225                 230                 235

<210> SEQ ID NO 105
<211> LENGTH: 21
<212> TYPE: PRT
<213> ORGANISM: Artificial Sequence
<220> FEATURE:
<223> OTHER INFORMATION: Synthetic Oligopeptide

<400> SEQUENCE: 105

Gly Ala Pro Gly Gly Gly Gly Ala Ala Ala Ala Gly Gly Gly
1               5                   10                  15

Gly Gly Gly Ala Pro
            20

<210> SEQ ID NO 106
<211> LENGTH: 39
<212> TYPE: PRT
<213> ORGANISM: Artificial Sequence
<220> FEATURE:
<223> OTHER INFORMATION: Synthetic Oligopeptide

<400> SEQUENCE: 106

Gly Ala Pro Gly Gly Gly Gly Gly Ala Ala Ala Ala Gly Gly Gly

```
                1               5                  10                  15
Gly Gly Gly Ala Pro Gly Gly Gly Gly Ala Ala Ala Ala Gly
                   20                  25                  30

Gly Gly Gly Gly Gly Ala Pro
                   35

<210> SEQ ID NO 107
<211> LENGTH: 57
<212> TYPE: PRT
<213> ORGANISM: Artificial Sequence
<220> FEATURE:
<223> OTHER INFORMATION: Synthetic Oligopeptide

<400> SEQUENCE: 107

Gly Ala Pro Gly Gly Gly Gly Ala Ala Ala Ala Gly Gly Gly
1               5                  10                  15

Gly Gly Gly Ala Pro Gly Gly Gly Gly Ala Ala Ala Ala Gly
                   20                  25                  30

Gly Gly Gly Gly Ala Pro Gly Gly Gly Gly Ala Ala Ala Ala
                   35                  40                  45

Ala Gly Gly Gly Gly Gly Ala Pro
       50                  55

<210> SEQ ID NO 108
<211> LENGTH: 475
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (475)..(475)
<223> OTHER INFORMATION: Xaa can be any naturally occurring amino acid

<400> SEQUENCE: 108

Met Gly Trp Ser Cys Ile Ile Leu Phe Leu Val Ala Thr Ala Thr Gly
1               5                  10                  15

Val His Ser Glu Leu Gln Leu Val Glu Ser Gly Gly Gly Leu Val Gln
                   20                  25                  30

Pro Gly Gly Ser Leu Arg Leu Ser Cys Ala Ala Ser Gly Phe Thr Phe
                   35                  40                  45

Ser Asp Tyr Ser Ala Ser Trp Val Arg Gln Ala Pro Gly Lys Gly Leu
       50                  55                  60

Glu Trp Val Ser Ala Ile Ser Trp Ser Gly Asp Ser Thr Tyr Tyr Ala
65                  70                  75                  80

Glu Ser Val Lys Gly Arg Phe Thr Ile Phe Arg Asp Asn Ser Lys Asn
                   85                  90                  95

Thr Leu Tyr Leu Gln Met Asn Ser Leu Arg Ala Glu Asp Thr Ala Val
                   100                 105                 110

Tyr Tyr Cys Ala Lys Ser Trp Ala Thr Pro Ile Glu Ser Leu Tyr Tyr
                   115                 120                 125

Tyr Gly Ser Asp Tyr Trp Gly Gln Gly Thr Leu Val Thr Val Ser Ser
       130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                   165                 170                 175

Phe Pro Glu Pro Val Thr Val Ser Trp Asn Ser Gly Ala Leu Thr Ser
                   180                 185                 190
```

```
Gly Val His Thr Phe Pro Ala Val Leu Gln Ser Ser Gly Leu Tyr Ser
            195                 200                 205
Leu Ser Ser Val Val Thr Val Pro Ser Ser Ser Leu Gly Thr Gln Thr
        210                 215                 220
Tyr Ile Cys Asn Val Asn His Lys Pro Ser Asn Thr Lys Val Asp Lys
225                 230                 235                 240
Lys Val Glu Pro Lys Ser Cys Asp Lys Thr His Thr Cys Pro Pro Cys
                245                 250                 255
Pro Ala Pro Glu Ala Ala Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Ser Arg Asp Glu
370                 375                 380
Leu Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
    450                 455                 460
Gln Lys Ser Leu Ser Leu Ser Pro Gly Lys Xaa
465                 470                 475

<210> SEQ ID NO 109
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 109

Glu Leu Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Ser Ala Ser Trp Val Arg Gln Ala Pro Gly Lys Gly Leu Glu Trp Val
        35                  40                  45
Ser Ala Ile Ser Trp Ser Gly Asp Ser Thr Tyr Tyr Ala Glu Ser Val
    50                  55                  60
Lys Gly Arg Phe Thr Ile Phe Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 110
<211> LENGTH: 234
<212> TYPE: PRT
<213> ORGANISM: Artificial Sequence
<220> FEATURE:

```
<223> OTHER INFORMATION: Synthetic Polypeptide
<220> FEATURE:
<221> NAME/KEY: misc_feature
<222> LOCATION: (234)..(234)
<223> OTHER INFORMATION: Xaa can be any naturally occurring amino acid

<400> SEQUENCE: 110

Met Gly Trp Ser Cys Ile Ile Leu Phe Leu Val Ala Thr Ala Thr Gly
1               5                   10                  15

Val His Ser Ser Tyr Glu Leu Thr Gln Pro Leu Ser Val Ser Val Ala
            20                  25                  30

Leu Arg Gln Ala Ala Lys Ile Thr Cys Gly Gly Asn Asn Ile Gly Ser
        35                  40                  45

Gln Thr Ala Gln Trp Tyr Gln Gln Lys Pro Gly Gln Ala Pro Val Leu
    50                  55                  60

Val Ile Tyr Ala Asn Asn Arg Arg Pro Ser Gly Ile Pro Glu Arg Phe
65                  70                  75                  80

Ser Gly Ser Lys Ser Gly Asn Thr Ala Thr Leu Thr Ile Ser Arg Ala
                85                  90                  95

Gln Ala Gly Asp Glu Ala Asp Tyr Tyr Cys Gln Val Trp Asp Ala Ser
            100                 105                 110

Thr Gln Ala Ile Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser Xaa
225                 230

<210> SEQ ID NO 111
<211> LENGTH: 19
<212> TYPE: PRT
<213> ORGANISM: Artificial Sequence
<220> FEATURE:
<223> OTHER INFORMATION: Synthetic Oligopeptide

<400> SEQUENCE: 111

Met Gly Trp Ser Cys Ile Ile Leu Phe Leu Val Ala Thr Ala Thr Gly
1               5                   10                  15

Val His Ser
```